US007253258B2

(12) United States Patent
Hooi

(10) Patent No.: US 7,253,258 B2
(45) Date of Patent: Aug. 7, 2007

(54) PROLINE RICH ACIDIC PROTEIN AND USES THEREOF

(75) Inventor: Shing Chuan Hooi, Singapore (SG)

(73) Assignee: National University of Singapore, Singapore (SG)

( * ) Notice: Subject to any disclaimer, the term of this patent is extended or adjusted under 35 U.S.C. 154(b) by 197 days.

(21) Appl. No.: 10/985,790

(22) Filed: Nov. 10, 2004

(65) Prior Publication Data
US 2007/0160596 A1 Jul. 12, 2007

Related U.S. Application Data

(60) Provisional application No. 60/518,883, filed on Nov. 10, 2003.

(51) Int. Cl.
C07K 1/00 (2006.01)
C12N 9/20 (2006.01)
C12N 15/00 (2006.01)
C12N 1/20 (2006.01)

(52) U.S. Cl. ............... 530/350; 435/252.3; 435/320.1; 435/69.1

(58) Field of Classification Search ............... 435/69.1, 435/252.3, 320.1; 530/350
See application file for complete search history.

(56) References Cited

OTHER PUBLICATIONS

Hao et al., pfluegers Archiv European Journal of Physiology, Mar. 2002, vol. 443, No. Supplement 1, pp. S252 print. Meeting info: 81st Annual Joint Meeting of the Physiological Society, the Scandinavian Physiological Society and the German Physiological Society, Tuebingen, Germany, Mar. 15-19, 2002.*
Brownwell, J.E. and Allis, C.D. Special HATs for special occasions: linking histone acetylation to chromatin assembly and gene activation. Curr Opin Genet. Dev, 6:176-184, 1996.
Cress, W.D. and Seto, E. Histone deacetylases, transcriptional control, and cancer. J Cell Physiol, 184:1-16, 2000.
Gray, S.G. and Ekstrom, T.J. The human histone deacetylase family. Exp Cell Res, 262:75-83,2001.
Grunstein, M. Histone acetylation in chromatin structure and transcription. Nature, 389:349-352, 1997.
Hark, A. T. et al., CTCF mediates methylation-sensitive enhancer-blocking activity at the H19/Igf2 locus. Nature 405:486-489, 2000.

(Continued)

Primary Examiner—Maryam Monshipouri
(74) Attorney, Agent, or Firm—Conley Rose, P.C.

(57) ABSTRACT

The present invention relates to isolated polynucleotide comprising a sequence selected from the group consisting of: (a) a polynucleotide comprising a sequence encoding the polypeptide SEQ ID NO:3 or a biologically active or immunogenic fragment thereof; (b) a polynucleotide comprising a sequence encoding the polypeptide SEQ ID NO:4 or a biologically active or immunogenic fragment thereof; (c) a polynucleotide which hybridises to a polynucleotide having a sequence complementary to that of the polynucleotide (a) and (b); and (d) a RNA equivalent to the sequences (a) to (c). The invention also provides methods of treatment and diagnosis of diseases associate with the repression or decreased expression of functional PRAP. In some instances, methods of treatment associated with the stimulation of cell proliferation is also provided, in particular, for the treatment of wounds.

3 Claims, 16 Drawing Sheets

```
  1    GGCCGGGTGCCAGATACTGGGATCAGCCACTGCAGCTCCCTGAGCACTCTCTACAGAGAC
              F0                                              prapF1
 61    GCGGACCCCAGACATGAGGAGGCTCCTCCTGGTCACCAGCCTGGTGGTTGTGCTGCTGTG
                       M  R  R  L  L  L  V  T  S  L  V  V  V  L  L       15
                        prapF2
121    GGAGGCAGGTGCAGTCCCAGCACCCAAGGTCCCTATCAAGATGCAAGTCAAACACTGGCC
        W  E  A  G  A  V  P  A  P  K  V  P  I  K  M  Q  V  K  H  W       35
181    CTCAGAGCAGGACCCAGAGAAGGCCTGGGGCGCCCGTGTGGTGGAGCCTCCGGAGAAGGA
        P  S  E  Q  D  P  E  K  A  W  G  A  R  V  V  E  P  P  E  K       55
                  prapR2                  prapR1            F3
241    CGACCAGCTGGTGGTGCTGTTCCCTGTCCAGAAGCCGAAACTCTTGACCACCGAGGAGAA
        D  D  Q  L  V  V  L  F  P  V  Q  K  P  K  L  L  T  T  E  E       75
301    GCCACGAGGTCAGGGCAGGGGCCCCATCCTTCCAGGCACCAAGGCCTGGATGGAGACCGA
        K  P  R  G  Q  G  R  G  P  I  L  P  G  T  K  A  W  M  E  T       95
361    GGACACCCTGGGCCGTGTCCTGAGCCCCGAGCCCGACCATGACAGCCTGTACCACCCTCC
        E  D  T  L  G  R  V  L  S  P  E  P  D  H  D  S  L  Y  H  P       115
                                                              R3
421    GCCTGAGGAGGACCAGGGCGAGGAGAGGCCCCGGTTGTGGGTGATGCCAAATCACCAGGT
        P  P  E  E  D  Q  G  E  E  R  P  R  L  W  V  M  P  N  H  Q       135
481    GCTCCTGGGACCGGAGGAAGACCAAGACCACATCTACCACCCCCAGTAGGGCTCCAGGGG
        V  L  L  G  P  E  E  D  Q  D  H  I  Y  H  P  Q                   151
541    CCATCACTGCCCCCGTTCTGTTCCAAAGCCCAAGCTGTTGGGACTGGGACCCTTCCTACC
               R0
601    CTGCCCCAGCTAGACAAATAAACCCCACAGGCCAAAAAAAAAAAAAAAA
```

OTHER PUBLICATIONS

Jenuwein, T. Re-SET-ting heterochromatin by histone methyltransferases. Trends Cell Biol, 11:266-273, 2001.

Jones, P.A. and Baylin, S.B., The fundamental role of epigenetic events in cancer, Nat. Rev. Genet., 3:415-428, 2002.

Jones, P.L. et al., Methylated DNA and MeCP2 recruit histone deacetylase to repress transcription. Nat. Genet., 19:187-191, 1998.

Kasik, J. and Rice, E., A novel complementary deoxyribonucleic acid is abundantly and specifically expressed in the uterus during pregnancy. Am J. Obstet Gynecol, 176:452-456, 1997.

Marks, P. et al., Histone deacetylases and cancer: causes and therapies. Nat. Rev. Cancer, 1:194-202, 2001.

Nan, X. et al., Transcriptional repression by the methyl-CpG-binding protein MeCP2 involves a histone deacetylase complex. Nature, 393:386-389, 1998.

Plass, C. et al., Identification of Grf1 on mouse chromosome 9 as an imprinted gene by RLGS-M. Nat. Genet., 14: 106-109, 1996.

Robertson, K.D. et al., DNMT1 forms a complex with Rb, E2F1 and HDAC1 and represses transcription from E2F-responsive promoters. Nat. Genet., 25:338-342, 2000.

Wolffe, A.P. and Pruss, D, Targeting chromatin disruption: Transcription regulators that acetylate histones. Cell, 84:817-819, 1996.

Yamashita, K. et al., Pharmacologic unmasking of epigenetically silenced tumor suppressor genes in esophageal squamous cell carcinoma. Cancer Cell, 2:485-495, 2002.

Zhang, J. et al., Characterization and expression of the mouse pregnant specific uterus protein gene and its rat homologue in the intestine and uterus. Biochim Biophys Acta, 1492:526-530, 2000.

* cited by examiner

FIGURE 1

```
1    GGCCGGGTGCCAGATACTGGGATCAGCCACTGCAGCTCCCTGAGCACTCTCTACAGAGAC
                         F0                            prapF1
61   GCGGACCCCAGACATGAGGAGGCTCCTCCTGGTCACCAGCCTGGTGGTTGTGCTGCTGTG
                   M  R  R  L  L  L  V  T  S  L  V  V  V  L  L    15
              prapF2
121  GGAGGCAGGTGCAGTCCCAGCACCCAAGGTCCCTATCAAGATGCAAGTCAAACACTGGCC
     W  E  A  G  A  V  P  A  P  K  V  P  I  K  M  Q  V  K  H  W   35

181  CTCAGAGCAGGACCCAGAGAAGGCCTGGGGCGCCCGTGTGGTGGAGCCTCCGGAGAAGGA
     P  S  E  Q  D  P  E  K  A  W  G  A  R  V  V  E  P  P  E  K   55
              prapR2            prapR1         F3
241  CGACCAGCTGGTGGTGCTGTTCCCTGTCCAGAAGCCGAAACTCTTGACCACCGAGGAGAA
     D  D  Q  L  V  V  L  F  P  V  Q  K  P  K  L  L  T  T  E  E   75

301  GCCACGAGGTCAGGGCAGGGGCCCCATCCTTCCAGGCACCAAGGCCTGGATGGAGACCGA
     K  P  R  G  Q  G  R  G  P  I  L  P  G  T  K  A  W  M  E  T   95

361  GGACACCCTGGGCCGTGTCCTGAGCCCCGAGCCCGACCATGACAGCCTGTACCACCCTCC
     E  D  T  L  G  R  V  L  S  P  E  P  D  H  D  S  L  Y  H  P   115
                                                       R3
421  GCCTGAGGAGGACCAGGGCGAGGAGAGGCCCCGGTTGTGGGTGATGCCAAATCACCAGGT
     P  P  E  E  D  Q  G  E  E  R  P  R  L  W  V  M  P  N  H  Q   135

481  GCTCCTGGGACCGGAGGAAGACCAAGACCACATCTACCACCCCCAGTAGGGCTCCAGGGG
     V  L  L  G  P  E  E  D  Q  D  H  I  Y  H  P  Q                151

541  CCATCACTGCCCCCGTTCTGTTCCAAAGCCCAAGCTGTTGGGACTGGGACCCTTCCTACC
            R0
601  CTGCCCCAGCTAGACAAATAAACCCCACAGGCCAAAAAAAAAAAAAAAAA
```

FIGURE 5
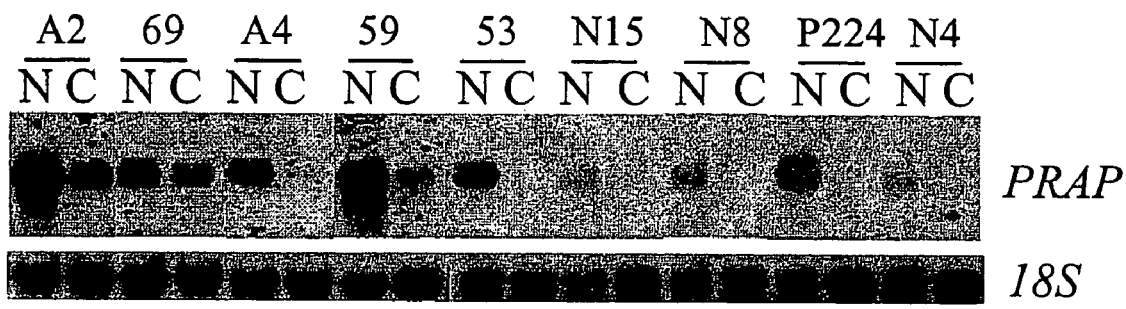
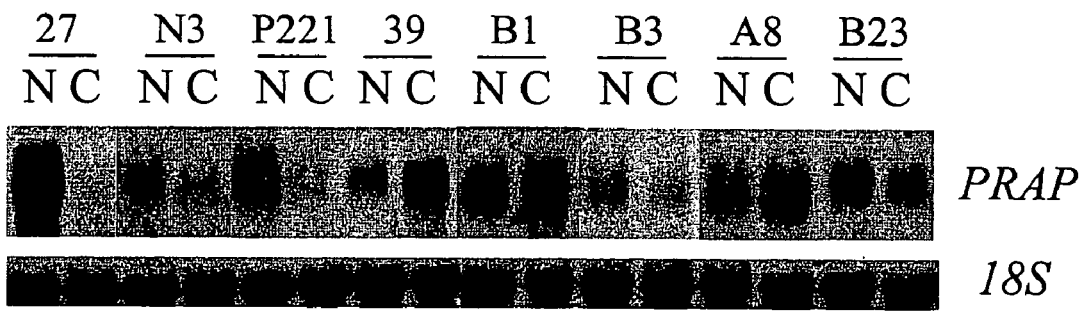

FIGURE 8

```
PR    MRRLLLVTSLVVVLLWEAGAVPAPKVPIKMQVKHWPSEQDPEK-AWGARVV

V1    MRRLLLVTSLVVVLLWEAGAVPAPKVPIKMQVKHWPSEQDPENRAWGARVV

V2    MRRLLLVTSLVVVLLWEAGAVPAPKVPIKMQVKHWPSEQDPEK-AWGARVV

PR    EPPEKDDQLVVLFPVQKPKLLTTEEKPRGQGRGPILPGTKAWMETEDTLG

V1    EPPEKDDQLVVLFPVQKPKLLTTEEKPRGQGRGPILPGTKAWMETEDTLG

V2    EPPEKDDQLVVLFPVQKPKLLTTEEKPRG---------TKAWMETEDTLG

PR    RVLSPEPDHDSLYHPPPEEDQGEERPRLWVMPNHQVLLGPEEDQDHIYHPQ

V1    HVLSPEPDHDSLYHPPPEEDQGEERPRLWVMPNHQVLLGPEEDQDHIYHPQ

V2    HVLSPEPDHDSLYHPPPEEDQGEERPRLWVMPNHQVLLGPEEDQDHIYHPQ

Figure 2 - PR=PRAP, V1=variant 1; V2=variant 2
```

← 633bp PROMO region

PROLINE RICH ACIDIC PROTEIN AND USES THEREOF

CROSS-REFERENCE TO RELATED APPLICATIONS

This application is a non-provisional application claiming priority to provisional application Ser. No. 60/518,883 filed on Nov. 10, 2003, which is hereby incorporated by reference.

FIELD OF THE INVENTION

The present invention relates to proline-rich acidic protein (PRAP) and PRAP isoforms and polynucleotides which identify and encode them. In addition, the invention provides expression vectors and host cells, agonists, antibodies. In particular, the invention provides methods for preventing or treating disorders associated with the expression of PRAP.

BACKGROUND OF THE INVENTION

The Proline-rich acidic protein (PRAP) gene was first identified in the mouse as a pregnant-specific uterine protein (psup) (Kasik and Rice, 1997). The gene was expressed in the mouse uterus from day 12 of pregnancy to the third day after parturition. Studies conducted in the laboratory demonstrated that PRAP expression was not limited to the late pregnant uterus (Zhang et al., 2000). PRAP mRNA was found abundantly expressed in the proximal small intestine of both the rat and mouse. Expression was highest in the proximal small intestine. Expression decreased distally and was undetectable in the terminal ileum in Northern blots.

The PRAP gene encodes a novel protein expressed at high concentrations in human kidney, liver and the gastrointestinal tract. It has no homology to known proteins. However, the presence of a signal peptide in the N-terminal part of the protein suggests that it is a secreted protein.

Epigenetic mechanisms are integral in to the process of tumour development (Jones and Bayin, 2002). Epigenetic modifications do not change the DNA sequence itself but alter the transcriptional activity of genes, changing the repertoire of genes expressed by the cell. The two major epigenetic mechanisms operating in the cell are DNA methylation at CpG islands in the promoter and histone acetylation. Methylation at CpG islands silences gene transcription in most instances (Hark et al., 2000), but, rarely, it results in activation (Hark et al., 2000; Plass et al., 1996). Similarly, deacetylation of histones is thought to result in transcriptional silencing because of the condensation of chromatin (Gray and Ekstrom, 2001; Cress and Seto, 2000; Wolffe and Pruss, 1996; Grunstein, 1997; Brownell and Allis, 1996). Recent evidence suggests that the two processes are related. Methylated DNA appears to preferentially associate with histone deacetylase protein complexes and histone methylases (Nan et al., 1998; Jones et al., 1998; Robertson et al., 2000). Histone methylation has been shown to result in DNA methylation (Tamaru et al., 2001; Jenuwein, 2001).

Epigenetic mechanisms play important roles in the regulation of genes involved in the development of cancer. Its importance is underscored by the reversal of the cancer phenotype when the cells are treated with drugs that modify epigenetic mechanisms (Marks et al., 2001; Johnstone, 2002; Marks et al., 2000). Genes that are epigenetically silenced during carcinogenesis are potential tumour suppressors. The identification of these genes facilitates the design of therapeutic strategies to combat cancer. There is therefore renewed interest to identify genes that are silenced in cancer, especially those involved in differentiation and cell proliferation (Yamashita et al., 2002).

U.S. Pat. No. 5,856,139 and US patent application 2002/0115153 describe a human PRAP gene and the encoded protein. These documents disclose the use of PRAP or PRAP agonists to stimulate cell proliferation. They also disclose the use of PRAP antagonists to treat cancer or prevent cell proliferation.

The role of PRAP in regulating cell proliferation has been very unclear to recommend specific treatment strategies using this molecule and therefore there is a demand for investigation which would clarify that role.

SUMMARY OF THE INVENTION

The present invention addresses the problems above. Further, the present invention has found that the mechanism of action of PRAP on cells, and therefore its practical utility in medicine, is diametrically opposite to that disclosed by the prior art.

More in particular, the invention relates to the use of PRAP, PRAP isoforms or variants and PRAP agonists for use as suppressors of cancer, cell or tissue proliferation and of inflammatory disorders. The present invention also provides novel PRAP isoforms.

According to one aspect, the invention provides a novel isolated polynucleotide comprising a sequence selected from the group consisting of:

a polynucleotide comprising a sequence encoding the polypeptide SEQ ID NO:3 or a biologically active or immunogenic fragment thereof;

a polynucleotide comprising a sequence encoding the polypeptide SEQ ID NO:4 or a biologically active or immunogenic fragment thereof;

a polynucleotide which hybridises to a polynucleotide having a sequence complementary to that of the polynucleotide (a) and (b);

a RNA equivalent to the sequences (a) to (c).

Polypeptides encoded by any of the polynucleotides above are also within the scope of the present invention. In particular, the polypeptide may be a polypeptide comprising the amino acid sequence SEQ ID NO:3 and/or SEQ ID NO:4 or a biologically active or immunogenic fragment thereof. At least one polypeptide may be comprised in a vector. At least one of the polypeptides as described above may be transformed in a cell. Alternatively, the at least one polypeptide may be comprised in a transgenic organism.

According to another aspect, the present invention provides a compound. In particular, the compound is an agonist of any polypeptide within the scope of the present invention.

Also provided is an isolated antibody which specifically binds to any polypeptide within the scope of the present invention.

The present invention also provides an isolated antibody which specifically binds to any agonist and/or antagonist within the scope of the present invention. More in particular, according to the one aspect, the antibody has a silencing effect by binding to PRAP or to a PRAP agonist, thereby increasing proliferation of cells to stimulate growth. According to another aspect, the antibody is used to bind PRAP, PRAP agonist and/or PRAP antagonist in a diagnostic method.

In particular, the antibody may be a monoclonal, polyclonal, chimeric, humanised, single chain, Fab, Fab', F(ab)' fragments and/or F(v) portions of the whole antibody.

The present invention also provides a vector comprising at least one polynucleotide as described above. Also provided is a cell which may be transformed with a recombinant polypeptide which is within the scope of the present invention. The cell may also be transformed with the vector comprising a polypeptide provided by the present invention.

Another aspect of the invention is a transgenic organism comprising at least one polypeptide within the scope of the present invention. Alternatively, the transgenic organism may comprise the vector, which in turn comprises at least one polypeptide. The transgenic organism may also comprise the cell with the vector.

According to another aspect, the present invention provides a method for producing any polypeptide described above, wherein the method comprises the steps of:
 a) culturing a cell under conditions suitable for expression of the polypeptide, wherein said cell is transformed with a recombinant polynucleotide, and said recombinant polynucleotide comprises a promoter sequence operably linked to a polynucleotide encoding the polypeptides; and
 b) recovering the polypeptide so expressed.

In particular, the polypeptide comprises the sequence of SEQ ID NO:3 and/or SEQ ID NO:4.

Another aspect is a method for detecting a target polynucleotide in a sample, said target polynucleotide having a sequence of a polynucleotide as described above or a polynucleotide comprising the sequence of SEQ ID NO:2, the method comprising the steps of:
 (a) hybridising the sample with a probe comprising at least 20 contiguous nucleotides comprising a sequence complementary to said target polynucleotide in the sample, and which probe specifically hybridises to said target polynucleotide, under conditions whereby a hybridisation complex is formed between said probe and said target polynucleotide or fragments thereof; and
 (b) detecting the presence or absence of said hybridisation complex, and, optionally, if present, the amount thereof.

In particular, the target polynucleotide comprises the sequence of SEQ ID NO:2, SEQ ID NO:3 and/or SEQ ID NO:4.

Another method that is provided by the present invention is a method for detecting a target polynucleotide in a sample, said target polynucleotide having a sequence of a polynucleotide according to any aspect of the present invention or a polynucleotide comprising the sequence SEQ ID NO:2, the method comprising:
 (a) amplifying said target polynucleotide or fragment thereof using polymerase chain reaction amplification; and
 (b) detecting the presence or absence of said amplified target polynucleotide or fragment thereof, and, optionally, if present, the amount thereof.

In particular, the target polynucleotide comprises the sequence of SEQ ID NO:2, SEQ ID NO:3 and/or SEQ ID NO:4.

According to another aspect, the present invention provides a composition, wherein the composition comprises at least one of the following:
 (a) a polypeptide comprising the polypeptide having the sequence of SEQ ID NO:3 or a biologically active immunogenic fragment thereof;
 (b) a polypeptide comprising the polypeptide having the sequence of SEQ ID NO:4 or a biologically active immunogenic fragment thereof;
 (c) an agonist of the polypeptide (a) and/or (b), or a biologically active or immunogenic fragment thereof.

Further, the composition may comprise a pharmaceutically acceptable excipient, diluent, and/or carrier or a combination thereof.

The present invention also provides a composition comprising at least one antibody according to any aspect of the present invention, and/or a pharmaceutically acceptable excipient, diluent, carrier or a combination thereof.

According to another aspect, it is provided a composition comprising an antisense oligonucletide capable of silencing any of the polynucleotide encoding PRAP or any isoform according to the invention.

Another aspect of the present invention is a method of treatment of a disease or condition associated with repression or decreased expression of functional PRAP, comprising administering to a subject in need thereof a composition as provided by any aspect of the invention. In particular, the method is for the treatment of cancer, hyperproliferative conditions and/or inflammation conditions. The composition may further comprise a polypeptide of SEQ ID NO:2 or a biologically active or immunogenic fragment thereof.

According to another aspect, the present invention provides a method for the stimulation of cell proliferation comprising administering an antibody against a PRAP or PRAP agonist or a fragment thereof to a mammal to increase proliferation of cells to stimulate growth. In particular, the method is for the stimulation of cell proliferation for the treatment and/or healing of wounds.

The invention also provides a method for the stimulation of cell proliferation comprising administering an antisense oligonucleotide against the polynucleotide, gene, or RNA encoding a PRAP or PRAP isoforms or PRAP agonist or a fragment thereof to a mammal to increase proliferation of cells to stimulate growth. In particular, the method is for the stimulation of cell proliferation for the treatment and/or healing of wounds. More in particular, this method comprises the use of RNAi technology.

The present invention also provides a diagnostic test for a condition or disease associated with the repression or decreased expression of PRAP in a biological sample, the method comprising:
 (a) combining the biological sample with an antibody against a PRAP or PRAP agonist or a fragment thereof; and
 (b) detecting an antibody:polypeptide fragment complex, wherein the absence of the complex indicates the absence of the polypeptide.

Another aspect of the present invention is a method of diagnosing a condition or disease associated with the repression or decreased expression of PRAP in a subject comprising:
 (a) obtaining a biological sample from the subject;
 (b) contacting the biological sample with an antibody against a PRAP or PRAP agonist or a fragment thereof, to form an antibody:polypeptide complex; and
 (c) detecting the complex,
wherein the absence of the complex correlates with the absence of the polypeptide in the biological sample, indicating the presence of the condition or disease associated with the repression or decreased expression of PRAP.

Accordingly, reference to PRAP in the methods may refer to a PRAP polypeptide encoded by a polynucleotide comprising a sequence selected from the group consisting of:
- (a) a polynucleotide comprising a sequence encoding the polypeptide SEQ ID NO:2 or a biologically active or immunogenic fragment thereof;
- (b) a polynucleotide comprising a sequence of SEQ ID NO:1;
- (c) a polynucleotide comprising a sequence encoding the polypeptide SEQ ID NO:3 or a biologically active or immunogenic fragment thereof;
- (d) a polynucleotide comprising a sequence encoding the polypeptide SEQ ID NO:4 or a biologically active or immunogenic fragment thereof;
- (e) a polynucleotide which hybridises to a polynucleotide having a sequence complementary to that of the polynucleotide (a), (b), (c) or (d) and which encodes a biologically active PRAP or an immunogenic fragment thereof; and
- (f) a RNA equivalent to the sequences (a) to (e).

Another aspect of the present invention provides a method for the diagnosis of cancer and/or abnormal cellular proliferation conditions comprising identifying PRAP mutations in tissues. In particular, the method may comprise identifying the methylation of PRAP promoter.

The present invention also provides a diagnostic kit comprising an antibody as described above that specifically binds to a polypeptide selected from a group consisting of:
- (a) a polypeptide comprising the amino acid sequence of SEQ ID NO:2 or an immunogenic fragment thereof;
- (b) a polypeptide comprising the amino acid sequence of SEQ ID NO: 3 or an immunogenic fragment thereof; and
- (c) a polypeptide comprising the amino acid sequence of SEQ ID NO:4 or an immunogenic fragment thereof.

The antibody may be a monoclonal, polyclonal, chimeric, humanised, single chain, Fab, Fab', F(ab)' fragments and/or F(v) portions of the whole antibody, and may optionally be in the form of a composition, further comprising a pharmaceutically acceptable excipient, vehicle, diluent, carrier or combination thereof.

The kit may also comprise an insoluble support, for example a solid support, upon which the antibody is fixed.

BRIEF DESCRIPTION OF THE FIGURES

FIG. 1: Nucleotide and predicted amino acid sequence of PRAP. The cDNA sequence and predicted open reading frame (single letter codes) are shown. Gene-specific primers used in the 5'- and 3'-RACE are indicated by arrows: forward primers prapF1 and prapF2, and reverse primers prapR1 and prapR2. The respective translation initiation and termination sites are indicated in bold. The primers used for the amplification of the probe for Northern hybridisations (F0 and R0) and real-time RT-PCR (F3 and R3) are indicated by arrows. The conserved GenBank expressed sequence tag sequence is shaded. Potential casein kinase II phosphorylation sites are boxed.

FIG. 5: Expression of PRAP in colorectal carcinomas. Northern blot showing PRAP expression in right colon cancers. Lanes N: normal colonic mucosa; Lanes C: carcinoma.

FIG. 6: Regulation of PRAP expression in butyrate-induced cell differentiation.

FIG. 7: Signal peptide of PRAP is cleaved in HeLa cells.

FIG. 8: This figure shows the amino acid sequences of PRAP (PR) and its variants (V1 and V2). The protein sequences are represented in one letter code. Hyphens have been introduced to optimise alignment.

FIG. 11: Proliferation of HT29 stable clones.

BRIEF DESCRIPTION OF SEQUENCES

Figure 2:
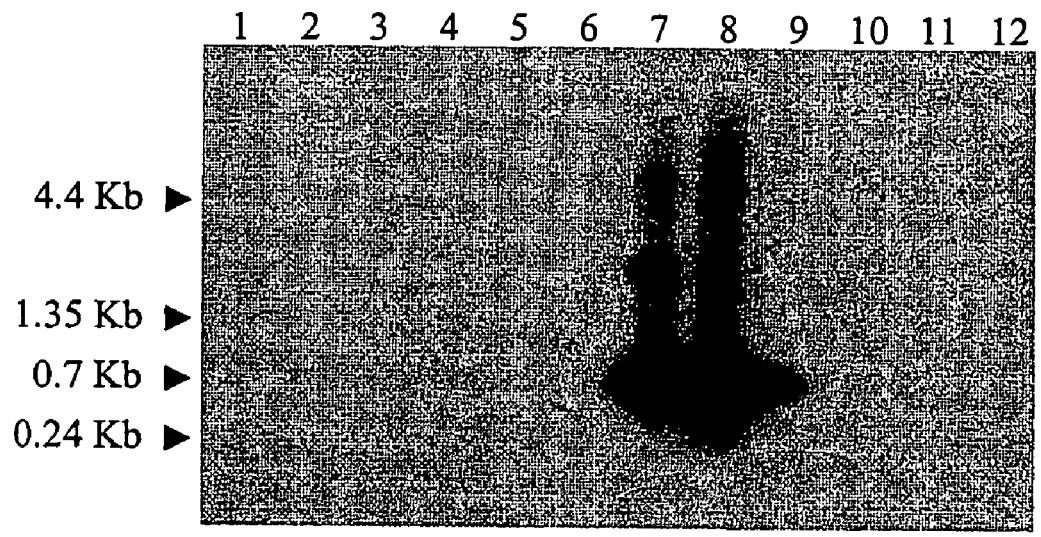
FIG. 2: Northern blot analysis of PRAP gene expression in human tissues. The human 12-lane MTN blot preloaded with 2 µg of purified polyadenylated RNA from different tissues was hybridised with PRAP probe. Lane 1: brain, Lane 2: heart, Lane 3: skeletal muscle, Lane 4: colon, Lane 5: thymus, Lane 6: spleen, Lane 7: kidney, Lane 8: liver, Lane 9: small intestine, Lane 10: placenta, Lane 11: lung, Lane 12: peripheral blood lymphocyte.

SEQ ID NO:1 is the gene sequence of the PRAP protein.
SEQ ID NO:2 is the amino acid sequence of PRAP protein.
SEQ ID NO:3 is the amino acid sequence of a novel isoform of the PRAP protein.
SEQ ID NO:4 is the amino acid sequence of another novel isoform of the PRAP protein.

DETAILED DESCRIPTION OF THE INVENTION

The cDNA sequence of Proline-rich acidic protein (PRAP) has previously been disclosed in U.S. Pat. No. 5,856,139 (herein incorporated by reference). This is shown here as SEQ ID NO:1. The protein encoded by this cDNA is referred to as SEQ ID NO:2. In the present invention, novel isoforms of the human PRAP were isolated. In particular, they were isolated by using a combination of real time polymerase chain reaction (RT-PCR) and 5' and 3' RACE. The isoforms resulted from the differential splicing of the PRAP gene. These isoforms have an amino acid sequence of SEQ ID NO:3 and SEQ ID NO:4 respectively. Further, it was shown that the PRAP was down-regulated epigenetically in cancers and that transfection of the isoforms resulted in growth suppression.

Accordingly, one aspect of the present invention provides an isolated polynucleotide comprising a sequence selected from the group consisting of:
(a) a polynucleotide comprising a sequence encoding the polypeptide SEQ ID NO:3 or a biologically active or immunogenic fragment thereof;
(b) a polynucleotide comprising a sequence encoding the polypeptide SEQ ID NO:4 or a biologically active or immunogenic fragment thereof;
(c) a polynucleotide which hybridises (under stringent conditions) to a polynucleotide having a sequence complementary to that of the polynucleotide (a) and (b);
(d) an RNA equivalent to the sequences (a) to (c).

According to another aspect, the present invention also encompasses a polypeptide encoded by a polynucleotide which is within the scope of the present invention. In particular, the polypeptide comprises an amino acid sequence of SEQ ID NO:3 and/or SEQ ID NO:4 or a biologically active or immunogenic fragment thereof.

Polynucleotide, as used herein, refers to cDNA, DNA, mRNA or RNA of genomic or synthetic origin which may be single- or double-stranded. Single-stranded DNA or RNA may be the coding strand, also known as the sense strand, or it may be the non-coding strand, also referred to as the antisense strand. Polynucleotide also includes nucleic acid molecules.

Isolated polynucleotide refers to a nucleic acid molecule, DNA or RNA, which has been removed from its natural environment. For example, recombinant DNA molecules contained in a vector are considered isolated for the purposes of the present invention. Further examples of isolated DNA molecules include recombinant DNA molecules maintained in heterologous host cells, and those DNA molecules purified (partially or substantially) from a solution whether produced by recombinant DNA or synthetic chemistry techniques. Isolated RNA molecules include in vivo or in vitro RNA transcripts of the DNA molecules of the present invention.

Polypeptides, as used herein refers to an amino acid sequence of a naturally occurring protein molecule, and terms such as 'amino acid sequence' or 'proteins' or the like are not meant to limit the amino acid sequence of the polypeptide to the complete, native amino acid sequence associated with the recited protein molecule.

PRAP, as used herein, refers to the amino acid sequences of substantially purified PRAP, its isoforms, their biologically active fragments thereof, or their immunogenic fragment thereof. PRAP, isoforms and their fragments according to the invention may be obtained from any species, particularly mammalian, including bovine, ovine, porcine, murine, equine, and preferably human, from any source whether natural, synthetic, semi-synthetic, or recombinant.

An isoform of PRAP refers to an amino acid sequence that is altered by one or more amino acids. The isoform may have "conservative" changes, wherein a substituted amino acid has similar structural or chemical properties, e.g., replacement of leucine with isoleucine. More rarely, an isoform may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software. The term variant may be used interchangeably with isoform.

Figure 12:
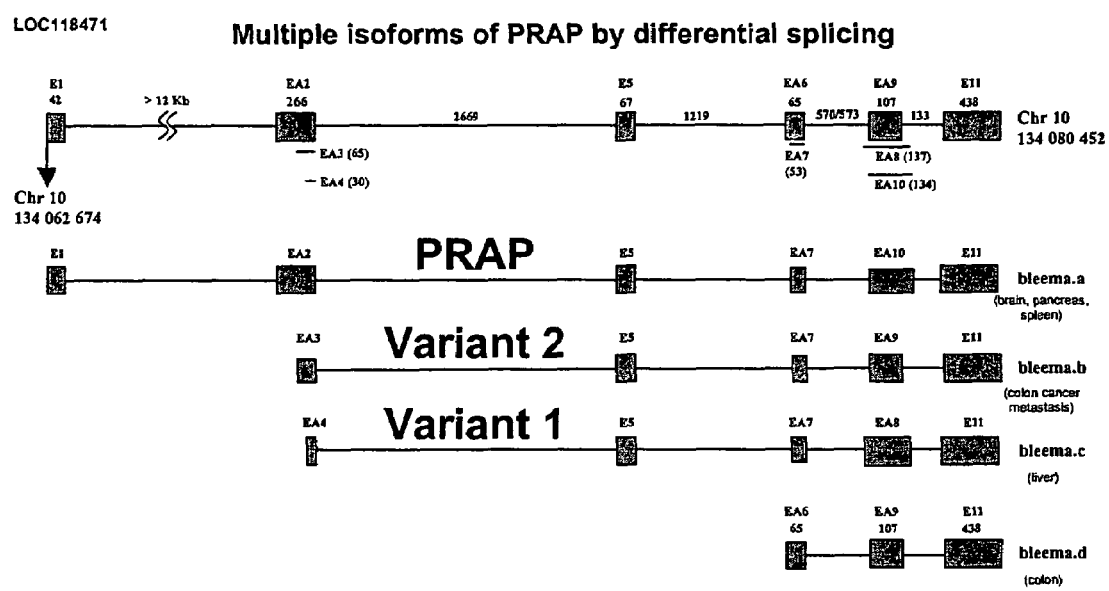
FIG. 12: This figure shows the multiple isoforms of PRAP by differential splicing.

The isoforms according to the invention encompass isoforms having an amino acid sequence of at least 80%, more preferably 90% amino sequence similarity to the PRAP amino acid sequence (SEQ ID NO:2). A most preferred PRAP isoform is one having at least 95% amino acid sequence similarity to SEQ ID NO:2. More in particular, the isoforms of the invention are those having the sequence identified in SEQ ID NO:3 and/or SEQ ID NO:4. The variants are isoforms generated by differential sequence. The genome structure of the PRAP gene is shown in FIG. 12. The PRAP gene is located on chromosome 10q26.

The term "biologically active", as used herein, refers to a protein having structural, regulatory, or biochemical functions of a naturally occurring molecule. Likewise, "immunogenic fragment" refers to the capability of the natural, recombinant, or synthetic fragment of PRAP, or any oligopeptide thereof, to induce a specific immune response in appropriate animals or cells and to bind with specific antibodies.

With reference to the polynucleotide (c), a nucleic acid "hybridises" to another polynucleotide (in the present case, a polynucleotide having a sequence complementary to that of polynucleotide (a) and (b)), when a single-stranded form of the polynucleotide can anneal to the other polynucleotide under appropriate conditions of temperature and solution ionic strength (Sambrook and Russell, Molecular Cloning, A Laboratory Manual, Cold Spring Harbour Laboratory Press, 2001). The conditions of temperature and ionic strength determine the "stringency" of the hybridisation. Hybridisation requires the two polynucleotides to contain complementary sequences. Depending on the stringency of the hybridisation, mismatches between bases are possible. The appropriate stringency for hybridising nucleic acids depends on the length of the polynucleotides and the degree of complementation, variables well known in the art. The greater the degree of similarity or homology between two polynucleotide sequences, the greater the value of Tm for hybrids of polynucleotides having those sequences. The relative stability (corresponding to higher Tm) of polynucleotide hybridisation decreases in the following order: RNA:RNA, DNA:RNA, DNA:DNA. For hybrids of greater than 100 nucleotides in length, equations for calculating Tm have been derived (Sambrook and Russell, 2001, as above). For hybridisation with shorter nucleic acids, i.e. oligonucleotides, the position of mismatches becomes more important, and the length of the oligonucleotide determines its specificity (Sambrook and Russell, 2001, as above). Preferably a minimum length for a hybridisable nucleic acid is at least about 10 nucleotides; more preferably at least about 15 nucleotides; most preferably the length is at least about 18 nucleotides.

According to another aspect of the present invention is a compound, wherein the compound is an agonist of any of the polypeptide which is within the scope of the present invention. In particular, the compound may be an agonist of a polypeptide comprising the amino acid sequence of SEQ ID NO:3 and/or SEQ ID NO:4 or a biologically active or immunogenic fragment thereof. The compound may also be an antagonist of any polypeptide within the scope of the present invention.

As used herein, the term agonist refers to a molecule which, when bound to PRAP, causes a change in PRAP which stimulates the activity of PRAP. Agonists may include proteins, nucleic acids, carbohydrates, or any other molecule that binds to PRAP.

The term antagonist, as used herein, refers to a molecule which, when bound to PRAP, blocks, inhibits or reduces the biological or immunological activity of PRAP. Antagonists and inhibitors may include proteins, nucleic acids, carbohydrates, or any other molecules which bind to PRAP.

Another aspect of the present invention provides for an isolated antibody which specifically binds to any polypeptide within the scope of the present invention. In particular, the antibody binds to a polypeptide comprising the amino acid sequence of SEQ ID NO:2, SEQ ID NO:3 and/or SEQ ID NO:4 or a biologically active or immunogenic fragment thereof.

According to a further aspect, the antibody may also bind specifically to an agonist as described herein.

An antibody is any immunoglobulin, including antibodies and fragments thereof, that bind to a specific epitope. The antibodies include, but are not limited to polyclonal, monoclonal, chimeric, humanised, single chain, Fab, Fab', F(ab)' fragments and/or F(v) portions of the whole antibody.

Various procedures known in the art may be used for the production of polyclonal antibodies to the polypeptides of the invention, or biologically active or immunogenic fragment thereof. For the production of antibody, various host animals can be immunised by injecting the polypeptide or a biologically active or an immunogenic fragment thereof, including but not limited to rabbits, mice, rats, sheep, goats, etc. In one embodiment, the peptide of the invention or fragment thereof can be conjugated to an immunogenic carrier, e.g., bovine serum albumin (BSA) or keyhole limpet hemocyanin (KLH). The peptide of the invention or immunogenic fragment may be further combined with any adjuvant known in the art (for example, Hood et al., in Immunology, p. 384, Second Ed., Benjamin/Cummings, Menlo Park, Calif., 1984, herein incorporated by reference).

For the preparation of monoclonal antibodies directed towards the polypeptide of the invention or biologically active or immunogenic fragment thereof, any technique that provides for the production of antibody molecules by continuous cell lines in culture may be used. These include, but are not limited to, the hybridoma technique originally developed by Kohler et al., Nature, 256:495-497 (1975), as well as the trioma technique, the human B-cell hybridoma technique (Kozbor et al., Immunology Today, 4:72, 1983), and the EBV-hybridoma technique to produce human monoclonal antibodies (Cole et al., in Monoclonal Antibodies and Cancer Therapy, pp. 77-96, Alan R. Liss, Inc., 1985). Immortal, antibody-producing cell lines can be created by techniques other than fusion, such as direct transformation of B lymphocytes with oncogenic DNA, or transfection with Epstein-Barr virus, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); also U.S. Pat. No. 4,341,761; U.S. Pat. No. 4,399,121; U.S. Pat. No. 4,427,783; U.S. Pat. No. 4,444,887; U.S. Pat. No. 4,451,570; U.S. Pat. No. 4,466,917; U.S. Pat. No. 4,472,500; U.S. Pat. No. 4,491,632; or U.S. Pat. No. 4,493,890.

In addition, techniques developed for the production of "chimeric antibodies" (Morrison, et al., 1984, Proc. Natl. Acad. Sci., 81, 6851-6855; Neuberger, et al., 1984, Nature 312, 604-608; Takeda, et al., 1985, Nature, 314, 452-454, incorporated herein by reference in their entirety) by splicing the genes from a mouse antibody molecule of appropriate antigen specificity together with genes from a human antibody molecule of appropriate biological activity can be used. For example, the genes from a mouse antibody molecule specific for an autoinducer can be spliced together with genes from a human antibody molecule of appropriate biological activity. A chimeric antibody is a molecule in which different portions are derived from different animal species, such as those having a variable region derived from a murine mAb and a human immunoglobulin constant region (See, e.g., Cabilly et al., U.S. Pat. No. 4,816,567; and Boss et al., U.S. Pat. No. 4,816,397, which are incorporated herein by reference in their entirety).

In addition, techniques have been developed for the production of humanised antibodies (See, e.g., Queen, U.S. Pat. No. 5,585,089 and Winter, U.S. Pat. No. 5,225,539, which are incorporated herein by reference in their entirety). An immunoglobulin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983), incorporated herein by reference in their entirety). Briefly, humanised antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423-426; Huston, et al., 1988, Proc. Natl. Acad. Sci. USA 85, 5879-5883; and Ward, et al., 1989, Nature 334, 544-546, incorporated herein by reference in their entirety) can be adapted to produce single chain antibodies against an immunogenic conjugate of the present invention. Single chain antibodies are formed by linking the heavy and light chain fragments of the Fv region via an amino acid bridge, resulting in a single chain polypeptide. Fab and F(ab')2 portions of antibody molecules may be prepared by the proteolytic reaction of papain and pepsin, respectively, on substantially intact antibody molecules by methods that are well-known. See for example, U.S. Pat. No. 4,342,566. Fab' antibody molecule portions are also well-known and are produced from F(ab')2 portions followed by reduction of the disulphide bonds linking the two heavy chain portions as with mercaptoethanol, and followed by alkylation of the resulting protein mercaptan with a reagent such as iodoacetamide.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffision assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting the binding of a secondary antibody or reagent to the primary antibody. In a further embodiment, the secondary antibody is labelled. Many means are known in the art for detecting the binding in an immunoassay and are within the scope of the present invention. For example, to select antibodies which recognise a specific epitope of a polypeptide of the invention (for example, any one of SEQ ID NOS:3 or 4), one may assay generated hybridomas for a product which binds to a polypeptide fragment containing such an epitope. For selection of an antibody specific to a polypeptide according to the invention from a particular species of animal, one can select on the basis of positive binding with the polypeptide of the invention expressed by or isolated from cells of that species of animal.

The terms "specific binding" or "specifically binding", refers to that interaction between a protein or polypeptide and an agonist, an antibody and an antagonist. The interaction is dependent upon the presence of a particular structure (i.e., the antigenic determinant or epitope) of the protein recognised by the binding molecule.

According to another aspect, the invention provides a vector comprising at least one of the nucleic acids (a), (b), (c) or (d). For example, the vector may comprise or be a bare nucleic acid segment, a plasmid, a phage, a virus, a viroid or a transposable element. The vector may further comprise a regulatory nucleic acid sequence linked to the nucleic acid encoding the polypeptide. The regulatory nucleic acid may be a prokaryotic or eukaryotic promoter.

The polynucleotides of the present invention may be joined to a vector containing a selectable marker for propagation in a host. Generally, a plasmid vector is introduced into mammalian or avian cells in a precipitate, such as a calcium phosphate precipitate, or in a complex with a charged lipid (e.g., LIPOFECTAMINE™; Life Technologies, Inc.; Rockville, Md.) or in a complex with a virus (such as an adenovirus; see U.S. Pat. Nos. 5,547,932 and 5,521, 291) or components of a virus (such as viral capsid peptides). If the vector is a virus, it may be packaged in vitro using an appropriate packaging cell line and then transduced into host cells. These host cells can be prokaryotic or eukaryotic host cells.

The expression vectors will preferably include at least one selectable marker. Such markers include, but are not limited to, dihydrofolate reductase (dhfr) or neomycin (neo) resistance for eukaryotic cell culture and tetracycline (tet) or ampicillin (amp) resistance genes for culturing in *E. Coli* and other bacteria.

Representative examples of appropriate hosts include, but are not limited to, bacterial cells, such as *Escherichia* spp. cells (particularly *E. coli*), *Bacillus* spp. cells particularly *B. cereus*, *B. subtilis* and *B. megaterium*), *Streptomyces* spp. cells, *Salmonella* spp. cells (particularly *S. typhimurium*) and *Xanthomonas* spp. cells; fungal cells, including yeast cells such as *Saccharomyces* spp. cells; insect cells such as *Drosophila* S2, *Spodoptera* Sf9 or Sf21 cells and *Trichoplusa* High-Five cells; other animal cells particularly mammalian cells and most particularly human cells such as CHO, COS, VERO, HeLa, myeloma cells, Bowes melanoma cells and HepG2 and other liver cell lines; and higher plant cells. Appropriate culture media and conditions for the above-described host cells are known in the art.

Among vectors preferred for use in bacteria include pQE70, pQE6 and pQE-9, available from Qiagen; pBS vectors, Phagescript vectors, Bluescript vectors, pNH8A, pNH16a, pNH18A and pNH46A, available from Stratagene; pcDNA3 available from Invitrogen; and pGEX, pTrxfus, pTrc99a, pET-5, pET-9, pKK223-3, pKK233-3. pDR540 and pRIT5 available from Pharmacia. Among preferred eukaryotic vectors are pWLNEO, pSV2CAT, pOG44, pXT1, pBK and pSG available from Stratagene; and pSVK3, pBPV, pMSG and pSVL available from Pharmacia. Other suitable vectors will be readily apparent to the skilled artisan.

Introduction of the vector into the host cell can be effected by various methods, which are described in many standard laboratory manuals, such as (Sambrook and Russell, 2001, as above). Alternatively, the polynucleotides may be transformed into a host cell directly. Further, the vector or polynucleotide (as the case may be) may be inserted into a transgenic organism.

Accordingly, another aspect of the invention is a host cell transformed with any polynucleotide of the present invention. The polynucleotides may be comprised within a vector, which is inserted into the host cell. The invention also provides a transgenic organism which comprises a recombinant polynucleotide according to any embodiment of the present invention. The polynucleotide may accordingly be comprised in a vector which is inserted into the transgenic organism. According to a further aspect, the vector may be comprised in a cell which is inserted into the transgenic organism.

The present invention also provides a method for producing the polypeptides of the present invention, the method comprising the steps of:

(a) culturing a cell under conditions suitable for expression of the polypeptide, wherein said cell is transformed with a recombinant polynucleotide, and said recombinant polynucleotide comprises a promoter sequence operably linked to a polynucleotide encoding the polypeptide; and (b) recovering the polypeptide so expressed.

The method for producing any polypeptide according to the invention also encompasses the method known as "gene activation", for example as the method developed by Transkaryotic Therapies Inc. (TKT) (see for example the method for the preparation of the TKT's erythropoietin, generally known with the brand name Dynepo), comprising introducing into a cell an exogenous DNA molecule to stimulate the production of an endogenous polypeptide.

In particular, the polypeptide may be a polypeptide comprising the amino acid of SEQ ID NO: 3 and/or SEQ ID NO:4.

The cell may be any suitable host cell as described above. In particular, the polynucleotide that expresses the polypeptide may be inserted into a vector, as described above, followed by introducing the vector into any suitable host cell.

Host cells transformed with the polynucleotides within the scope of the present invention may be cultured under conditions suitable for the expression and recovery of the protein from cell culture. The protein produced by a recombinant cell may be secreted or contained intracellularly depending on the sequence and/or the vector used. As will be understood by those skilled in the art, expression vectors containing polynucleotides which encode the polypeptides desired may be designed to contain signal sequences which direct secretion of those polypeptides through a prokaryotic or eukaryotic cell membrane. Other recombinant constructions may be used to join sequences encoding the polypeptides to nucleotide sequence encoding a polypeptide domain which will facilitate purification of soluble proteins. Such purification facilitating domains include, but are not limited to, metal chelating peptides such as histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and PRAP may be used to facilitate purification.

Another aspect of the present invention is a method for detecting a target polynucleotide in a sample, said target polynucleotide having a sequence of any polynucleotide within the scope of the present invention or a polynucleotide encoding a polypeptide comprising the amino acid sequence SEQ ID NO:2, the method comprising:
(a) hybridising the sample with a probe comprising at least 20 contiguous nucleotides comprising a sequence complementary to said target polynucleotide in the sample, and which probe specifically hybridises to said target polynucleotide, under conditions whereby a hybridisation complex is formed between said probe and said target polynucleotide or fragments thereof; and
(b) detecting the presence or absence of said hybridisation complex, and optionally, if present, the amount thereof.

In particular, the target polynucleotide encoding a polypeptide comprising the amino acid sequence of SEQ ID NO:2, SEQ ID NO: 3 and/or SEQ ID NO:4, or a biologically active or immunogenic fragment thereof.

The present invention also provides a method for detecting a target polynucleotide in a sample, said target polynucleotide having a sequence of any polynucleotide within the scope of the present invention or a polynucleotide encoding a polypeptide comprising the amino acid sequence SEQ ID NO:2, the method comprising:
(a) amplifying said target polynucleotide or fragment thereof using polymerase chain reaction amplification or any other amplification method known in the art; and
(b) detecting the presence or absence of said amplified target polynucleotide or fragment thereof, and, optionally, if present, the amount thereof.

In particular, the target polynucleotide encodes a polypeptide comprising the amino acid sequence of SEQ ID NO:2, SEQ ID NO: 3 and/or SEQ ID NO:4.

Polynucleotides may be used for diagnostic purposes. The polynucleotides which may be used include oligonucleotide sequences, antisense RNA and DNA molecules, and PNAs. The polynucleotides may be used to detect target polynucleotides (for example, the polynucleotides within the scope of the present invention, as well as polynucleotide comprising SEQ ID NO:1) and quantitate gene expression in tissue samples in which expression of PRAP may be correlated with disease. The diagnostic assay may be used to distinguish between absence, presence, and excess expression of PRAP, and to monitor regulation of PRAP levels during therapeutic intervention.

In one aspect, hybridisation with PCR probes which are capable of detecting polynucleotide sequences, including genomic sequences, encoding the polypeptides within the scope of the present invention, as well as the polypeptide comprising the amino acid sequence of SEQ ID NO:2, or closely related molecules, may be used to identify nucleic acid sequences which encode PRAP. The specificity of the probe, whether it is made from a highly specific region, e.g., 10 unique nucleotides in the 5' regulatory region, or a less specific region, e.g., especially in the 3' coding region, and the stringency of the hybridisation or amplification (maximal, high, intermediate, or low) will determine whether the probe identifies only naturally occurring sequences encoding PRAP, alleles, or related sequences.

Means for producing specific hybridisation probes for DNAs encoding PRAP include the cloning of nucleic acid sequences encoding PRAP or PRAP derivatives into vectors for the production of mRNA probes. Such vectors are known in the art, commercially available, and may be used to synthesise RNA probes in vitro by means of the addition of the appropriate RNA polymerases and the appropriate labelled nucleotides. Hybridisation probes may be labelled by a variety of reporter groups, for example, radionuclides such as 32P or 35S, or enzymatic labels, such as alkaline phosphatase coupled to the probe via avidin/biotin coupling systems, and the like.

Another aspect of the present invention is a composition comprising at least one of the following:
(a) a polypeptide comprising a sequence encoding the polypeptide SEQ ID NO:3 or a biologically active immunogenic fragment thereof;
(b) a polypeptide comprising a sequence encoding the polypeptide SEQ ID NO:4 or a biologically active immunogenic fragment thereof;
(c) an agonist of the polypeptide (a) or (b), or a biologically active or immunogenic fragment thereof.

Further, the composition optionally comprises a pharmaceutically acceptable excipient, diluent, and/or a carrier or a combination thereof.

The composition may also comprise a polypeptide of SEQ ID NO:2 or a biologically active or immunogenic fragment thereof.

According to another aspect, the present invention provides a composition comprising at least one antibody of any embodiment of the invention. The composition may further comprise a pharmaceutically acceptable excipient, diluent, carrier or a combination thereof.

Examples of suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen.

Compositions of the invention are administered by any suitable means, directly (e.g., locally, as by injection, implantation or topical administration to a tissue locus) or systemically (e.g., parenterally or orally). Where the compositions of the invention are to be provided parenterally, such as by intravenous, subcutaneous, opthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration, the composition preferably comprises part of an aqueous or physiologically compatible fluid suspension or solution.

In particular, the compositions may be delivered to cancer cells through injection or by injecting vectors capable of directing PRAP expression in eukaryotic cells. Alternatively, the composition may be administered in capsules to protect against digestion in the stomach and small intestine to target delivery to tumours in the large intestine. Different means of delivery can be designed and modified depending on the location of the tumour. This would be apparent to one skilled in the art.

According to another aspect, the present invention provides a method of treatment of a disease or condition associated with repression or decreased expression of functional PRAP, comprising administering to a subject in need thereof the composition according to any embodiment of the invention. In particular, the composition comprises a polypeptide of SEQ ID NO:2, SEQ ID NO:3 and/or SEQ ID NO:4 or a biologically active or immunogenic fragment thereof. In particular, the method is for the treatment of cancer, hyperproliferative conditions and/or inflammation conditions.

Cancer refers to, but not limited to, adenocarcinoma, sarcomas, lymphomas, leukemia, and cancers of the bladder, bone, brain, breast, colon, heart, kidney, liver, lung, ovary, pancreas, paraganglia, parathyroid, prostate, skin, intestine, testis, thyroid, tongue, and uterus cancer.

Inflammation conditions refer to, but not limited to, AIDS, Addison's disease, allergies, asthma, bronchitis, Crohn's disease, dermatomyositis, diabetes mellitus, emphysema, Graves' disease, irritable bowel syndrome, lupus erythematosus, myasthenia gravis, multiple sclerosis, urethritis, rheumatoid and osteoarthritis, thyroiditis, and ulcerative colitis.

Yet another aspect of the present invention is a method for the stimulation of cell proliferation comprising administering a composition comprising any antibody or an antisense oligonucleotide (for example, a siRNA oligonucleotide) of any embodiment of the present invention against PRAP or PRAP agonist or a fragment thereof to a mammal to increase proliferation of cells to stimulate growth. In particular, the method if for the treatment of wounds.

The reduction or inhibition of activity of PRAP, PRAP isoforms, or biologically or immunogenic active fragments thereof can also be obtained either in vivo or in vitro inhibiting, delaying or repressing the expression of the PRAP gene encoding the PRAP polypeptide, isoforms, or fragments thereof. The term PRAP herein encompasses isoforms and fragments thereof. Accordingly, the invention provides a method which comprises inhibiting, delaying or repressing the expression of the PRAP gene. As a particular example, the invention provides a method which comprises inhibiting, delaying or repressing the expression of PRAP mRNA. Accordingly, the method comprises administering to or transfecting in vivo or in vitro cells with a nucleic acid construct comprising a nucleic acid molecule binding or hybridising to the PRAP gene and/or PRAP mRNA, isoforms or to a portion thereof. The nucleic acid molecule is complementary or substantially complementary to the PRAP gene and/or PRAP mRNA.

Accordingly, the present invention extends to the preparation of antisense nucleotides and ribozymes that may be used to interfere with the expression of the PRAP polypeptides at the translational level. This approach involves antisense nucleic acid molecules and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule (Weintraub, Sci. Am., 262:4046 (1990); Marcus-Sekura, Anal. Biochem., 172:289-295, 1988). In the cell, they hybridise to that mRNA, forming an untranslatable double-stranded molecule. Therefore, antisense nucleic acids interfere with the expression of mRNA into protein. Oligomers of about fifteen nucleotides and molecules that hybridise to the AUG initiation codon will be particularly efficient, since they are easy to synthesise and are likely to pose fewer problems than larger molecules when introducing them into PRAP peptide-producing cells. Antisense methods have been used to inhibit the expression of many genes in vitro [(Marcus-Sekura, 1988 supra; Hambor et al., J. Exp. Med., 168:1237-1245 (1988)].

Ribozymes are RNA molecules possessing the ability to specifically cleave other single-stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, J. Am. Med. Assoc., 260: 3030-3034, 1988). Because they are sequence-specific, only mRNAs with particular sequences are inactivated.

For example, the nucleic acid molecule is an antisense DNA and/or RNA molecule. The nucleic acid molecule may be an antisense single strand RNA (sRNA), double strand RNA (dsRNA), double strand DNA (dsDNA), double strand hybrid RNA/DNA (RNA/DNA), small interfering RNA (siRNA) and/or ribozymes. The nucleic acid construct can be any suitable vector, phage, plasmid, a nucleic acid fragment or the like comprising the nucleic acid molecule.

There is no limit to the size of the nucleic acid construct and the nucleic acid molecule. In particular, the nucleic acid molecule is 15-40 nucleotides, in particular 18-30 nucleotides, more in particular 18-25 nucleotides, for example 19-23 nucleotides.

PRAP silencing using antisense technology leads to an increase of cell proliferation. An application of this technology is that of wound healing.

For the purposes of methods of treatment according to any embodiment of the invention, PRAP refers to a PRAP polypeptide encoded by a polynucleotide comprising a sequence selected from the group consisting of:
(a) a polynucleotide comprising a sequence encoding the polypeptide SEQ ID NO:2 or a biologically active or immunogenic fragment thereof;
(b) a polynucleotide comprising a sequence comprising SEQ ID NO:1;
(c) a polynucleotide comprising a sequence encoding the polypeptide SEQ ID NO:3 or a biologically active immunogenic fragment thereof;
(d) a polynucleotide comprising a sequence encoding the polypeptide SEQ ID NO:4 or a biologically active immunogenic fragment thereof;

(e) a polynucleotide which hybridises to a polynucleotide having a sequence complementary to that of the polynucleotide (a), (b), (c) or (d); and (f) an RNA equivalent to the sequences (a) to (e).

The present invention also provides a diagnostic test for a condition or disease associated with the repression or decreased expression of PRAP in a biological sample, the method comprising:

(a) combining the biological sample with an antibody according to any embodiment of the present invention against a PRAP or PRAP agonist or a fragment thereof; and (b) detecting an antibody:polypeptide fragment complex, wherein the absence of the complex indicates the absence of the polypeptide.

For the purposes of any diagnostic test or method as described herein, PRAP refers to a PRAP polypeptide encoded by a polynucleotide comprising a sequence selected from the group consisting of:

(a) a polynucleotide comprising a sequence encoding the polypeptide SEQ ID NO:2 or a biologically active or immunogenic fragment thereof;

(b) a polynucleotide comprising a sequence comprising SEQ ID NO:1;

(c) a polynucleotide comprising a sequence encoding the polypeptide SEQ ID NO:3 or a biologically active immunogenic fragment thereof;

(d) a polynucleotide comprising a sequence encoding the polypeptide SEQ ID NO:4 or a biologically active immunogenic fragment thereof;

(e) a polynucleotide which hybridises to a polynucleotide having a sequence complementary to that of the polynucleotide (a), (b), (c) or (d); and (f) an RNA equivalent to the sequences (a) to (e).

An example of a disease where PRAP is repressed or experiences decreased expression is cancer. PRAP is a tumour suppressing gene. PRAP will not be expressed in a person suffering from cancer. It would therefore be advantageous to use the antibody of the present invention for the early detection of cancer. For example, a biological sample is obtained from a human, and that sample is tested against the antibody of the present invention according to the diagnostic test described above. If it is found that the antibody does not bind to any epitope, it shows that PRAP is not present, indicating that the human is suffering from cancer.

Accordingly, the present invention also provides a method of diagnosing a condition or disease associated with the repression or decreased expression of PRAP in a subject comprising:

(a) obtaining a biological sample from the subject;

(b) contacting the biological sample with an antibody according to any embodiment of the present invention against PRAP or PRAP agonist or a fragment thereof, to form an antibody:polypeptide complex; and (c) detecting the complex, wherein the absence of the complex correlates with the absence of the polypeptide in the biological sample, indicating the presence of the condition or disease associated with the repression or decreased expression of PRAP.

The present invention also provides a method for the diagnosis of cancer and/or abnormal cellular proliferation conditions comprising identifying PRAP mutations in tissues. In particular, the method may comprise identifying the methylation of the PRAP promoter.

Another aspect of the present invention is a diagnostic kit comprising any antibody according to any embodiment of the present invention that specifically binds to a polypeptide selected from a group consisting of:

(a) a polypeptide comprising the amino acid sequence of SEQ ID NO:2, or an immunogenic fragment thereof;

(b) a polypeptide comprising the amino acid sequence of SEQ ID NO:3, or an immunogenic fragment thereof; and (c) a polypeptide comprising the amino acid sequence of SEQ ID NO:4, or an immunogenic fragment thereof.

Accordingly, the kit may comprise the antibody fixed onto an insoluble support, for example a solid support. The diagnostic kit may also comprise the antibody in the form of frozen or lyophilised (freeze-drying) antibodies, or antibody fragments to be reconstituted, respectively, by thawing (optionally followed by further dilution) or by suspension in a (preferably buffered) liquid vehicle. The kits may also include buffer and/or excipient solutions (in liquid or frozen form), or buffer and/or excipient powder preparations to be reconstituted with water, for the purpose of mixing with the antibodies for use for diagnosis purposes. Preferably, the kit may also comprise instructions for reconstituting and using the antibodies for the detection of diseases, for example, for the detection of cancer. The buffers, excipients and other component parts can be sold separately or together with the kit.

Having now generally described the invention, the same will be more readily understood through reference to the following examples which are provided by way of illustration, and are not intended to be limiting of the present invention.

EXAMPLES

Example 1

Materials and Methods

Standard molecular biology techniques known in the art and not specifically described were generally followed as described in Sambrook and Russel, Molecular Cloning: A Laboratory Manual, Cold Springs Harbor Laboratory, New York (2001).

5'- and 3'-RACE to Identify cDNA Ends

The cloning and characterisation of the rat prap gene has been previously described (Zhang et al., 2000). Using the rat sequence, a BLAST search of the NCBI GenBank database was performed and several human EST sequences that were more than 50% homologous to a region of the rat prap gene were identified. Two pairs of primers (prapF1, prapR1 and prapF2, prapR2) were designed based on the approximately 180 bp of conserved sequence (shaded in FIG. 1) to amplify the 5'- and 3'-ends of the PRAP cDNA using the SMART RACE cDNA Amplification Kit (Clontech, Palo Alto, Calif.). In brief, 1 µg total RNA obtained from human normal colon mucosa was reverse transcribed using primers provided in the kit. The 5'-end of human PRAP was amplified by 2 rounds of nested PCR using gene specific primer prapR1, prapR2 and universal primer mix (UPM) and nested universal primer (NUP), respectively (FIG. 1). UPM and NUP were provided in the kit. Similarly, the 3' end of PRAP was amplified by 2 rounds of nested PCR using the 3' specific primer prapF1, prapF2 and UPM, NUP, respectively. The products of 5' and 3' RACE were purified and cloned into pTOPO vector (Invitrogen, The Netherlands). The cDNA inserts were sequenced using a Rhodamine Terminator Cycle sequencing Ready Reaction Kit (PE Applied Biosystems, Foster City, Calif.) and an ABI Prism 377 Autosequencer.

End-to-End Amplification of Full Length PRAP cDNA

In order to confirm the presence of full length PRAP, 3 µg of total RNA prepared from normal colon mucosa was used for RT-PCR. Forward Primer F0 and reverse primer R0 (FIG. 1) were used for the PCR reaction after reverse-transcription with oligo-dT. The product was gel purified and sequenced three times. It was used as a probe for Northern blot analysis.

Tissue Samples

Anonymised human tissue specimens were obtained from the archives of the tumour bank of National University Hospital of Singapore. Non-tumour tissues were obtained adjacent to the margin of resection (at least 5 cm away from tumour). Necrotic parts of the tumours were removed. Colonic mucosa was dissected away from muscle and connective tissue. The samples were snap frozen in liquid nitrogen and stored at −80° C. The remaining tissues were sent for histopathological analysis.

Cell Lines and Treatments

The HT29, HCT116, HepG2 and HeLa cell lines were purchased from American Type Culture Collection (Manassas, Va.). HT29 and HCT116 cells were cultured in McCoy's 5A (Sigma Chemical Co., St. Louis, Mo.), HepG2 in DMEM and HeLa in RPMI, all supplemented with 10% fetal bovine serum (Life Technologies, Inc., Gaithersburg, Md.), at 37° C. in a 5% $CO_2$ humidified atmosphere. Cells were treated with 5 mM sodium butyrate (final concentration in media; Life Technologies, Inc) or vehicle. Total RNA was prepared from the cells at the respective time points from three separate flasks.

In a separate experiment, HT29 and HCT116 cells were treated with either vehicle, 5-aza-2' deoxycytidine (DAC, 1 µM; Sigma), trichostatin A (TSA, 300 nM; Sigma) or a combination of both drugs for 72 hours. For the combined treatment, cells were treated with 1 µM DAC for 24 h followed by the addition of 300 nM TSA for another 48 h. Total RNA was extracted using the RNase Kit (Qiagen). The experiment was performed in duplicates and the average result calculated.

Northern Blot Analysis

A multi-tissue blot comprising poly-A RNA derived from various human tissues was used (MTN blot #7780-1, Clontech, Palo Alto, Calif.) to determine the expression of PRAP in human tissues. In a separate experiment, total RNA from tissues and cell lines was prepared using the guanidinium thiocyanate method as previously described (MacDonald et al., 1987). 15 µg of RNA was separated by formaldehyde/agarose gel electrophoresis, transferred to nylon membrane (Qiabrane, Qiagen, Hilden, Germany), cross-linked (Stratalinker, Stratagene, La Jolla, Calif.), and hybridised to cDNA probes, as previously described (Wang et al., 1999). The probes were obtained by labelling PCR amplified PRAP cDNAs with $^{32}P$ using the random priming method. Relative mRNA levels were quantified by Typhoon phospho-imager (Amersham Bioscience, UK) and normalised against 18S levels. Normal/Tumour (N/T) ratios were obtained by dividing the normalised relative densitometric units of the normal mucosa by tumour.

Real Time Quantitative RT-PCR

Primers for real-time PCR were designed using the LightCycler Probe Design Software, version 1.0 (Roche, France). F3 and R3 were used for the amplification of PRAP (FIG. 1). Real-time PCR was performed on the LightCycler (Roche, France) using the LightCycler-RNA amplification Kit SYBR Green I (Roche, France). The specificity of the amplification was assessed by electrophoretic separation of the amplified products and melting curve analysis. Standard curves of PRAP and GAPDH were constructed using serial dilutions of total RNA from 0.1-500 ng. The efficiencies of both amplifications were calculated according to the slope of the standard curves. Relative PRAP expression was quantified after normalisation with GAPDH.

Expression in Prokaryotic Cells

To express His-PRAP in *E. coli*, full length PRAP sequence was cloned into pET vector. This was then transformed into competent *E. coli* (XL1 Blu). PRAP+ clones were picked and verified for the PRAP sequence via miniprep followed by restriction digest.

The recombinant vector was then transformed into *E. coli* (BL21). Clones were picked and 5 mL liquid cultures were done. These were induced with IPTG to express His-PRAP. Thereafter, clones having the highest expression were identified by SDS-PAGE with Coomassie Blue staining. Large scale liquid culture using this clone then gives the required His-PRAP, which was purified by affinity chromatography on a Ni-NTA column.

Expression in Insect Cells

The BaculoDirect™ expression from Invitrogen was used. This system facilitates the direct transfer of the gene of interest into the baculoviral genome in vitro without the need for additional cloning or recombination in bacterial or insect cells. The resultant recombinant baculoviral DNA is transfected directly into insect cells to generate recombinant virus for expression.

Full length PRAP (based on sequence in FIG. 1) was cloned into a Gateway™ vector to create an "entry" clone. A lambda recombination reaction was performed in vitro to generate recombinant baculovirus DNA containing the PRAP coding sequence. Insect cells were transfected with the recombinant baculovirus DNA to generate baculovirus (P1 stock). Several rounds of infection were performed to generate higher viral titres. The P6 stock was used for expression of PRAP. The recombinant protein was secreted into the supernatant and purified using a Ni-NTA system based on the His tag at the C-terminal end of the recombinant protein.

Generation of Polyclonal Antibody

Polyclonal antibodies against recombinant GST-PRAP (amino acid 21-150) (GST is glutathione S-transferase) were raised in New Zealand white female rabbits and affinity-purified against GST-PRAP immobilised on nitrocellulose membrane. The specific antibodies were eluted using IgG elution buffer (Pierce Biotechnology, Rockford, Ill.) and neutralised with 0.1 volume of 1M Tris base.

Generation of Monoclonal Antibody

To begin the generation of monoclonal antibody, balb/c mice were immunised with the recombinant protein HIS-PRAP (HIS=histone) over a period of 10 weeks. Their spleen cells were harvested and fused with myeloma cells (Sp2/0-Ag14). Selection media was used to ensure that only the hybridoma cells survive. The positive clones were then picked and tested for their ability to secrete our PRAP-specific antibody by ELISA. The clones that give the highest titer were cultured. The culture medium was purified to obtain the monoclonal antibody. In parallel to this in vitro production technique, the hybridoma cells were also injected into the peritoneal cavity of Balb/c mice. Ascitic fluid developed over a period of 2 to 3 weeks and was tapped.

Immunohistochemistry

Anonymised, archived samples of human kidney, liver, colon and uterine cervix were obtained from patients with surgical resection. Tissues were formalin-fixed, paraffin-embedded, sectioned and mounted on slides. Deparaffinized slides were treated with 3% hydrogen peroxide in phosphate-buffered saline and pre-treated at 96° C. for 30 minutes in 10 μmol/L citrate buffer (pH 6.0). A rabbit polyclonal antibody specific to PRAP (1:1000 dilution) was the primary antibody. Staining was carried out by an avidin-biotinylated horseradish peroxidase complex method (DAKO, Glostrup, Denmark) using a goat-anti-rabbit secondary antibody. The PRAP antibody (1 μg/ml) pre-incubated with 10 μg/ml of GST-PRAP was used as a control.

Western Blot Analysis

Cells or tissues were extracted with RIPA buffer (1×PBS, 1% Nonidet P-40, 0.5% sodium deoxychelate and 0.1% SDS. Protease inhibitors: PMSF, aprotinin, pepstatin A and leupeptin were freshly added to the RIPA buffer at the point of usage). 5 μg of total protein was separated on 12% SDS polyacrylamide gel and blotted onto the Hybond™-C extra nitrocellulose membrane (Amersham Life Science). The primary antibody used was a rabbit polyclonal antibody specific for PRAP (1:5000) or mouse monoclonal antibody specific for GAPDH (Chemicon International, Temecula, Calif.). The secondary antibody was either HRP-conjugated anti-rabbit IgG (BioRad, Hercules, Calif., 1:10,000) or HRP-conjugated anti-mouse antibody (Santa Cruz Biotechnology, Santa Cruz, Calif., 1:20,000). The proteins were visualized using the SuperSignal® West Dura Extended (Pierce) chemiluminescent substrate and exposed to an autoradiograph film.

ELISA

For the detection of PRAP in the culture supernatant, pcDNA3.1-PRAP and pcDNA3.1 empty vector were transfected into HepG2 cells in a T25 flask. After 24 hours, the medium was replaced by serum free medium containing 1% Insulin-Transferrin-Selenium (Life technologies) in DMEM. The cultures were incubated for another 48 h and the supernatant was collected and passed through a 0.22 μm filter. The cleared supernatant was then concentrated 5-fold in a spin vacuum and used for coating the ELISA plates. Different volumes of supernatant from the two transfections were used for coating the plate. PRAP polyclonal antibody at a dilution of 1:1000 was used as the primary antibody.

Isolation and Identification of PRAP Isoforms in Normal Tissues

3 μg RNA was extracted from normal colon mucosa and liver. RT-PCR was performed using oligo-dT and specific PRAP primers. The primers used were F0 and R0 (FIG. 1). The amplified products were ligated into T-vector plasmid (Promega, Madison, Wis.). Ten positive clones from each sample were randomly selected and sequenced.

Cloning and Overexpression of PRAP Isoforms in Different Cell Lines

PRAP and its two major isoforms (PRAPV1 and PRAPV2, that is SEQ ID NO:3 and SEQ ID NO:4, respectively) were cloned into the BamHI and EcoRI sites of the pcDNA 3.1 vector (Invitrogen, Carlsbad, Calif.). The PRAP/-SP plasmid was generated by amplifying the PRAP coding sequence beginning from amino acid 21 to 151. The cDNA fragment was cloned into pcDNA 3.1. All plasmids were sequenced to confirm identity and exclude mutations. The plasmids were transfected into HepG2 and HeLa cells using Lipofectamine (Invitrogen), according to manufacturer's recommendations. Each experiment was performed in quadruplicates and repeated three times. After 72 h, the cells were harvested and counted by a haemocytometer after Trypan Blue staining. Whole cell extracts were prepared for Western blot analysis as described.

Colony Formation Assay and Generation of Stable Clones

HeLa cells were transfected with either 1 μg of pcDNA3.1/PRAP or pcDNA 3.1 using Lipofectamine plus reagent (Invitrogen). Cells were subjected to selection in 1200 μg/ml G418 and the number of colonies scored manually at the end of 3 weeks. Stable clones of HT29 cells expressing PRAP were selected in a similar way. We managed to expand 2 clones out of the 22 selected. The expression of PRAP was confirmed by Western Blot analysis.

Cell Proliferation Study by MTT Method

Stable clones of HT29 cells expressing PRAP were seeded in 24 well plates in McCoys'5A medium supplemented with 10% FBS. The colorimetric MTT (3-(4,5-dimethylthiazol-2yl)-2,5-diphenyl-tetrazolium bromide; Sigma) assay was used as a surrogate measure of cell number at various time points. The experiment was performed in replicates of six and repeated twice.

Identification of PRAP Promoter Methylation

DNA methylation is an important epigenetic modification which plays a vital role during the early steps involved in tumour progression. Methylation of promoter regions of many tumour suppressor genes, DNA repair genes and metastasis inhibitor genes have been linked to gene silencing and consequently to cancer. Mostly, methylation is confined to cytosines of the CpG dinucleotide, which is base-paired exactly to the same sequence (in the reverse orientation) in the reverse strand of the DNA.

Two pieces of evidence suggested that the PRAP promoter may be methylated. Firstly, PRAP expression was downregulated in cancers. Secondly, the gene was upregulated by treatment with 5' deazacytidine (DAC), a drug that inhibits methylation. We looked at the methylation status of the PRAP promoter in HT29 cells (colon cancer cell line). Two regions upstream of the first exon of PRAP were found to be CG-rich. These were named UP and PROMO. These regions were targeted for methylation specific enzyme digestion.

Results

Cloning and Sequence Analysis of Human PRAP

We identified and sequenced 633 bp of the human PRAP cDNA (FIG. 1). The sequence has been deposited in GenBank (GenBank Accession No. AF421885). The cDNA encoded a putative protein of 151 amino acids that was about 50% homologous to that of rat and mouse pregnant specific uterus protein (PSUP) (GenBank accession no. U28486). There are two regions of the protein that showed a higher degree of conservation. The N-terminus of the protein, predicted to be the signal peptide by the SignalP program (Nielsen et al., 1997) was more than 70% conserved between human and rodent. The C-terminal 135-149 aa was 80% conserved between human and rodent. The predicted cleavage site of the protein was between amino acid 20 and 21. Two putative casein kinase II phosphorylation sites were identified by the PROSITE program (FIG. 1).

Tissue Distribution of Human PRAP

Figure 3:
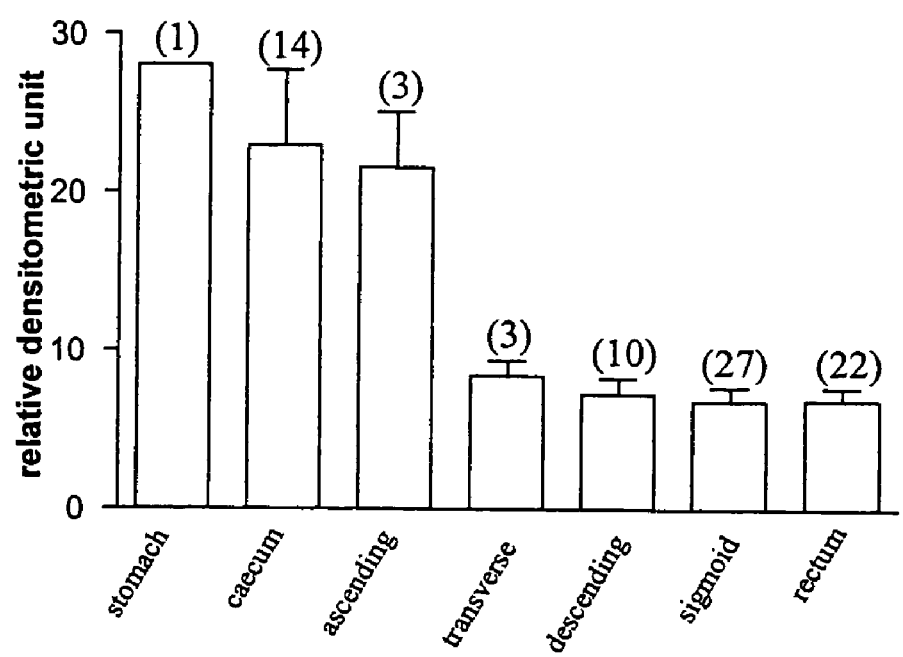
FIG. 3: Expression of PRAP in gastrointestinal tract (GI). Summary of Northern blot data showing PRAP expression in normal mucosa of GI. The number of samples in each group (from stomach) is indicated above the bars. The relative densitometric units shown were expressed against 18S to correct for minor loading differences.
Figure 4A:
FIG. 4A-H: Immunohistochemistry of human tissues. Tissue slides of human kidney (A and E), liver (B and F), colon mucosa (C and G), and cervix (D and H) were incubated with 1 µg/ml polyclonal antibody against PRAP (A-D) and PRAP polyclonal antibody (1 µg/ml) preincubated with 10 µg/ml GST-PRAP (E-H).
Figure 4B:
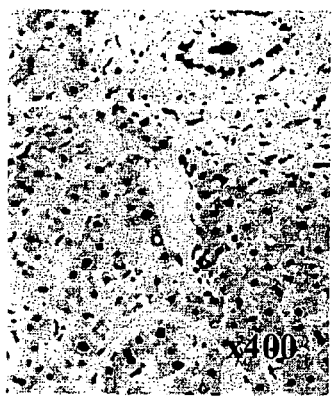
Figure 4C:
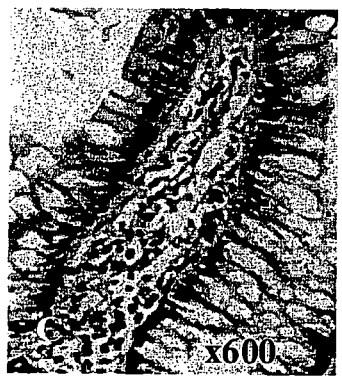
Figure 4D:
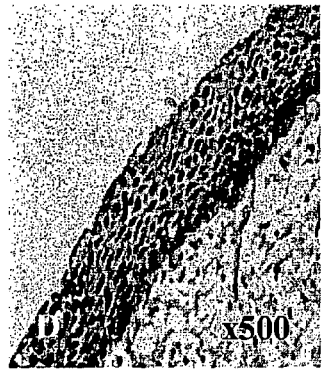
Figure 4E:
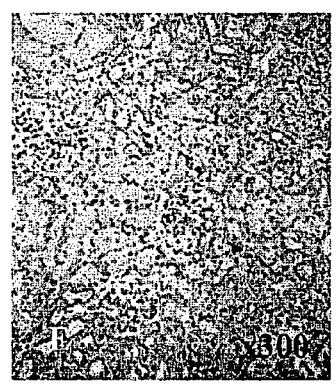
Figure 4F:
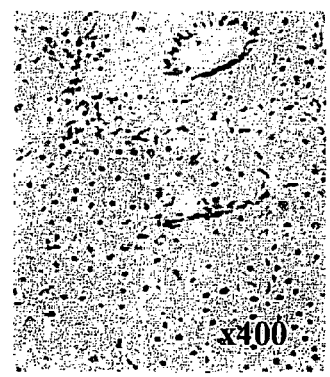
Figure 4G:
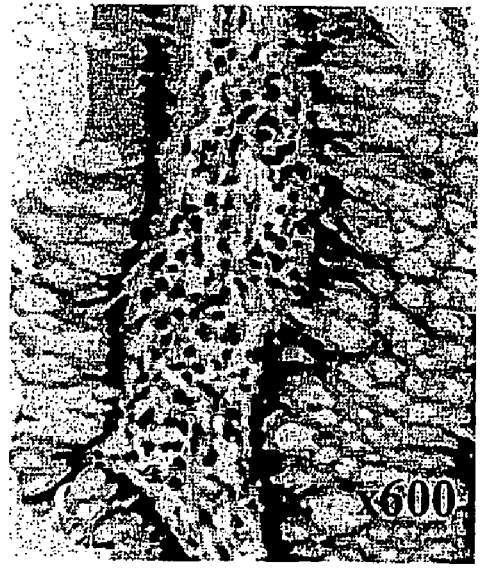
Figure 4H:
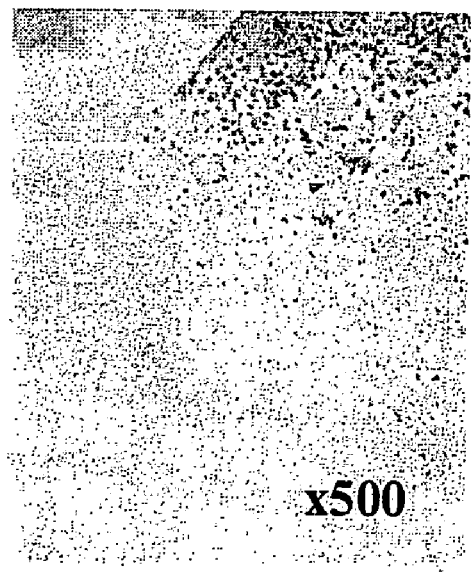

Northern Blot analysis showed hybridisation to a specific band around 700 bp in length. PRAP was abundantly expressed in liver and kidney, less in small intestine and colon. PRAP mRNA was not detected in the rest of the tissues (FIG. 2). In a separate study, we found high levels of PRAP in the mucosal layer of the stomach, caecum and ascending colon. A summary of the expression in the stomach and colon is shown in FIG. 3. The difference between expression in the caecum and distal colon was about 3.5-fold. The expression of PRAP was studied by immunohistochemistry (FIG. 4). Results showed that PRAP was expressed in the epithelial lining of the colon and cervix. PRAP was strongly expressed in the hepatocytes of the liver. Both the proximal and distal tubules were strongly stained for PRAP in the kidney. There was no expression of PRAP in the kidney glomerular cells.

PRAP Expression is Down-Regulated in Two Types of Cancers

We studied the regulation of PRAP gene expression in colorectal and liver cancers. Our earlier results indicated that PRAP was highly expressed in the right colon (caecum and ascending) and liver. Seventeen paired samples of right colon carcinoma and adjacent normal mucosa were randomly selected from a tissue bank. FIG. 5 shows the expression of PRAP in the seventeen pairs of samples. Although the basal level of PRAP expression showed substantial variation among the samples, PRAP expression was down-regulated in fourteen out of the seventeen sets of samples. In several cases, PRAP expression in the cancer samples was barely detectable by Northern blot analysis. Overall, PRAP expression was decreased 3.5-fold (P<0.01) in tumour tissues compared to matched normal mucosa. Real time RT-PCR was used to quantify the expression of PRAP in liver carcinomas. The efficiencies of PRAP and GAPDH amplifications were comparable at 2.0 and 2.2 respectively. The expression of PRAP was determined for nine sets of hepatocarcinomas and matched "normal" (non-tumour containing) liver tissue. Results are shown in Table 1. Overall, there was a 3.8-fold reduction of PRAP expression in hepatocarcinoma compared to matched "normal" livers (p<0.01).

TABLE 1

PRAP expression in 9 hepatocarcinoma samples. N/T ratio is the ratio of PRAP gene expression in normal against tumour tissue after normalisation with GAPDH

| Sample | N/T Ratio |
| --- | --- |
| 1 | 2.35 |
| 2 | 4.05 |
| 3 | 12.91 |
| 4 | 3.65 |
| 5 | 1.65 |
| 6 | 1.23 |
| 7 | 4.79 |
| 8 | 0.85 |
| 9 | 2.39 |
| Average | 3.77 ± 1.23 |

Regulation of PRAP expression by butyrate and epigenetic modifiers

Figure 6A:
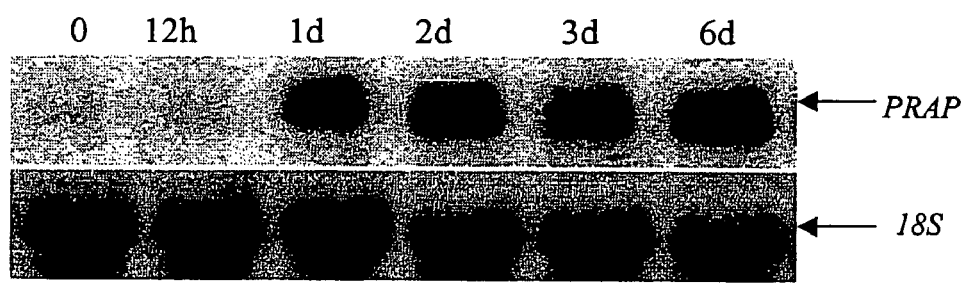
FIG. 6A: Northern blot showing PRAP expression in HT29 cells treated with 5 mM sodium butyrate for 0, 12, 24 h, 2 days, 3 days and 6 days. Hybridisation of Northern blots to 18S is shown in FIG. 6B.
Figure 6B:
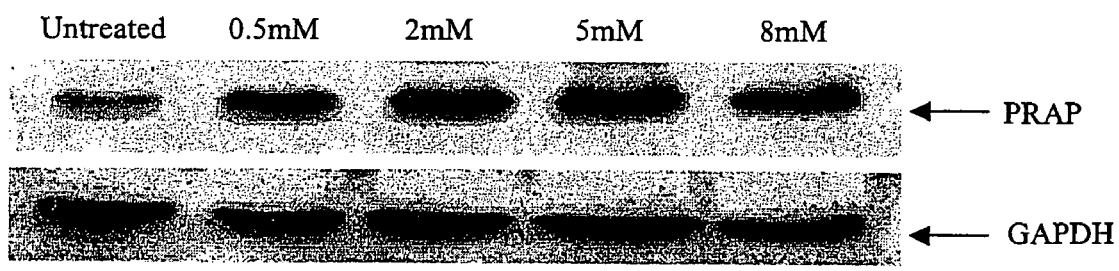
FIG. 6B shows the Western blot showing PRAP expression in response to different concentrations of sodium butyrate. GADPH was used as an internal control.

We studied the regulation of PRAP gene expression in HT29 cells by butyrate. Treatment of HT29 cells with 5 mM butyrate has been shown to induce cell differentiation within 24 h after treatment (McBain et al., 1997; Heerdt et al., 1997; Hodin et al., 1996; Augeron and Laboisse, 1984). PRAP gene expression was significantly increased 20-fold within 24 h after butyrate treatment (FIG. 6). The increase in expression was sustained for up to 6 days after treatment, at which time the cells were beginning to show morphological differentiation. The expression of the PRAP gene at this time was 29-fold higher than in control non-treated cells (FIG. 6A). Using Western blot analysis, we showed that butyrate treatment resulted also in an increase in PRAP expression (FIG. 6B). Maximal PRAP expression was observed between 2-5 mM of butyrate treatment.

To determine whether PRAP gene expression was regulated by epigenetic mechanisms, HT29 and HCT116 cells were treated with 1 μM DAC, which blocks DNA methylation, or 300 nM TSA to inhibit HDAC or both. PRAP expression was determined by a sensitive and specific quantitative RT-PCR and the results are shown in Table 2. Treatment of cells with 300 ng of TSA resulted in an 8.4-fold increase in PRAP expression in HT29 cells. Similarly, treatment of DAC resulted in an 8.5-fold increase in PRAP expression in the cells. Combined treatment with both TSA and DAC did not result in a further increase in PRAP expression. Interestingly, DAC treatment alone did not result in an increase in PRAP gene expression in HCT116 cells. However, HCT116 cells treated with TSA showed a 5.2-fold increase in PRAP gene expression. The combined treatment with both DAC and TSA resulted in a synergistic 19.3-fold increase in PRAP gene expression.

TABLE 2

PRAP expression in HT29 and HCT116 treated with TSA and DAC Real time RT-PCR results of PRAP expression in HT29 and HCT116 treated with TSA, DAC or in combination for 72 h.

|  |  | TSA (300 ng) | DAC (1 μm) | TSA & DAC |
| --- | --- | --- | --- | --- |
|  | HT29 (untreated) |  |  |  |
| $PRAP^{cp}$-$GAPDH^{cp}$ | 12.63 | 9.38 | 9.37 | 9.39 |
| Fold of increase | — | 8.4 | 8.5 | 8.3 |
|  | HCT116 (untreated) |  |  |  |
| $PRAP^{cp}$-$GAPDH^{cp}$ | 13.97 | 11.6 | 13.8 | 9.7 |
| Fold of increase | — | 5.17 | 1.11 | 19.29 |

[a]$PRAP^{cp}$-$GAPDH^{cp}$: crossing point of PRAP normalized by GAPDH (after normalization with efficiencies of PRAP and GAPDH, respectively).
[b]Fold increase: Fold increase of PRAP expression relative to untreated HT29 or HCT116.

PRAP is secreted

Figure 7A:
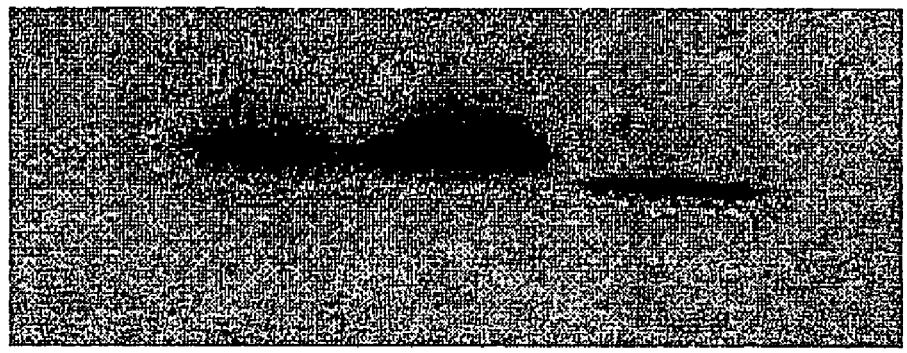
FIG. 7A shows HeLa cells which were transfected with PRAP, encoding full-length PRAP (Lane 1); PRAP/-SP, encoding PRAP without signal peptide (Lane 2); and PRAP/-29, encoding PRAP with 29 amino acids truncated from the $NH_2$-terminal (Lane 3).
Figure 7B:
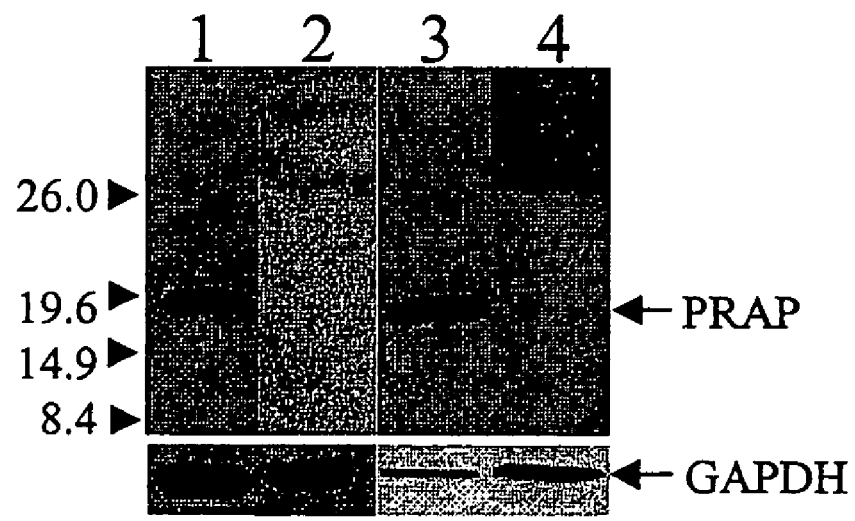
FIG. 7B shows a Western blot showing the specificity of polyclonal antibody against PRAP. 5 µg of liver lysate was loaded in each lane. The blot was incubated with anti-PRAP antibody 0.2 µg/ml (Lane 1), anti-PRAP antibody preincubated with 2 µg/ml GST-PRAP (Lane 2), anti-PRAP antibody preincubated with 2 µg/ml GST (Lane 3), and 0.2 µg/ml IgG from preimmune serum (Lane 4). The membranes were stripped and reprobed with anti-GAPDH monoclonal antibodies.

PRAP, PRAP/-SP and PRAP/-29 were transfected into HeLa cells. Western blot analysis showed that PRAP and PRAP/-SP transfected cells expressed a protein of similar size (FIG. 7A). This suggests that the signal peptide present in the full length PRAP was cleaved. PRAP/-29 transfected cells expressed a protein that was evidently smaller than PRAP and PRAP/-SP. FIG. 7B shows the specificity of the PRAP polyclonal antibody. Transfection of PRAP into HepG2 cells resulted in the secretion of PRAP into the supernatant (Table 3).

TABLE 3

Detection of PRAP in cluture medium of PRAP-transfected HeLa cells by ELISA. The ELISA readings of HeLa cell culture medium 72 h after transfection with pcDNA vector or pcDNA-PRAP. Different volumes of the culture medium were coated on ELISA plate. PRAP was detected with polyclonal antibody against PRAP (0.5 μg/ml).

| Volume of culture medium | 20 μl | 50 μl | 100 μl |
| --- | --- | --- | --- |
| Vector | 0.0713 | 0.0633 | 0.0533 |
| PRAP | 0.5273 | 0.6513 | 1.2313 |

Identification of PRAP variants in colon and liver

PRAP was amplified from normal colon and liver to identify PRAP isoforms present in these tissues. We randomly selected 10 clones each from colon and liver. The results are summarised in Table 4. About 45% of the 20 clones were identified as PRAP, 15% PRAPV1, 25% PRAPV2 and 15% others. PRAPV1 had an extra 3 bp inserted at position 201 bp of the PRAP coding sequence. The 3 bp insertion was predicted to result in a change in amino acid at position 42 from lysine to asparagine and arginine (42K to NR substitution/insertion). The 3 bp insertion resulted from a variation in the splicing between exon 3 and 4 (alternative exon EA7 to EA8, according to nomenclature in GenBank) of the PRAP genome (GenBank LocusID 118471, NCBI Aceview). PRAPV2 is also a splice variant that had 27 bp deleted from bp 309 to 335 of the coding region, also due to a variation in splicing between exon 3 and 4 (alternative EA7 to EA9). The deletion is predicted to generate a 9 amino acid deletion in PRAP. The other variants identified were single base differences that resulted in an amino acid change and likely represent polymorphisms among individuals. FIG. 8 shows a comparison of PRAP and the variants.

TABLE 4

Number of transcripts of PRAP and its variants in human normal colon mucosa and liver. The RT-PCR products of PRAP from normal colon mucosa and liver were cloned into pGEM-T vector. 10 positive (white) clones were randomly selected for sequencing. The number of clones or percentage of PRAP, PRAPV1 and PRAPV2 are indicated. 'Others' indicate sequences different from PRAP, PRAPV1 and PRAPV2.

|  | PRAP | PRAPV1 | PRAPV2 | OTHERS |
|---|---|---|---|---|
| COLON | 4 | 3 | 2 | 1 |
| LIVER | 5 | 0 | 3 | 2 |
| TOTAL | 9 (45%) | 3 (15%) | 5 (25%) | 3 (15%) |

Overexpression of PRAP and variants decreased cell numbers and colony formation

Figure 9A:
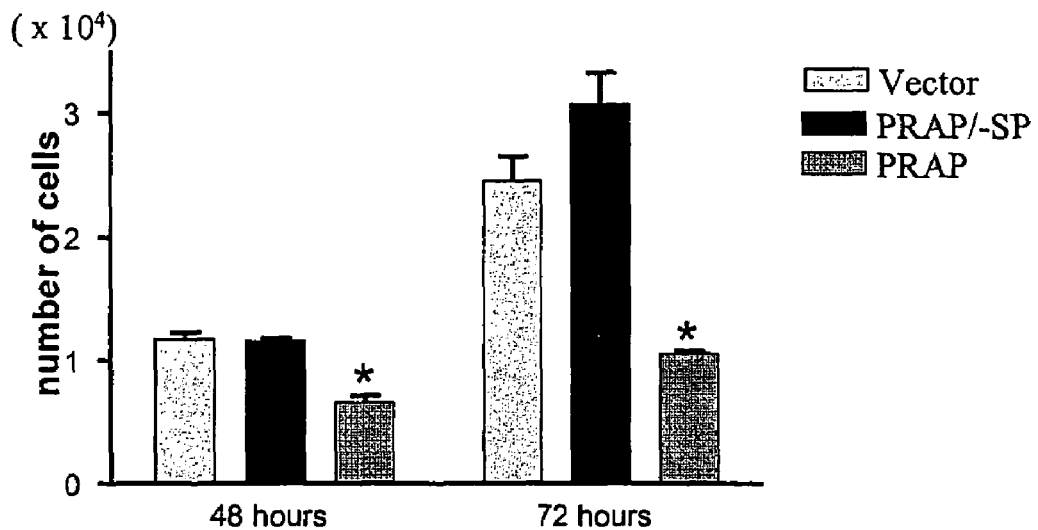
FIG. 9A shows HeLa cells transfected with Vector, PRAP and PRAP/-SP at 48 h and 72 h. Four transfections were done for each plasmid. *, $P<0.01$, relative to vector control.
Figure 9B:
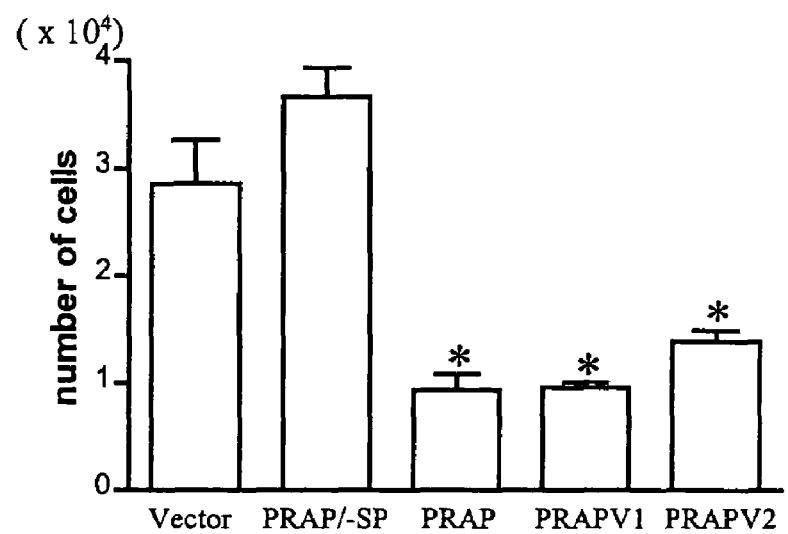
FIGS. 9B and C show HeLa and HepG2 cells transfected with vector, PRAP/-SP, PRAP, PRAPV1 and PRAPV2, respectively for 72 h.
Figure 9C:
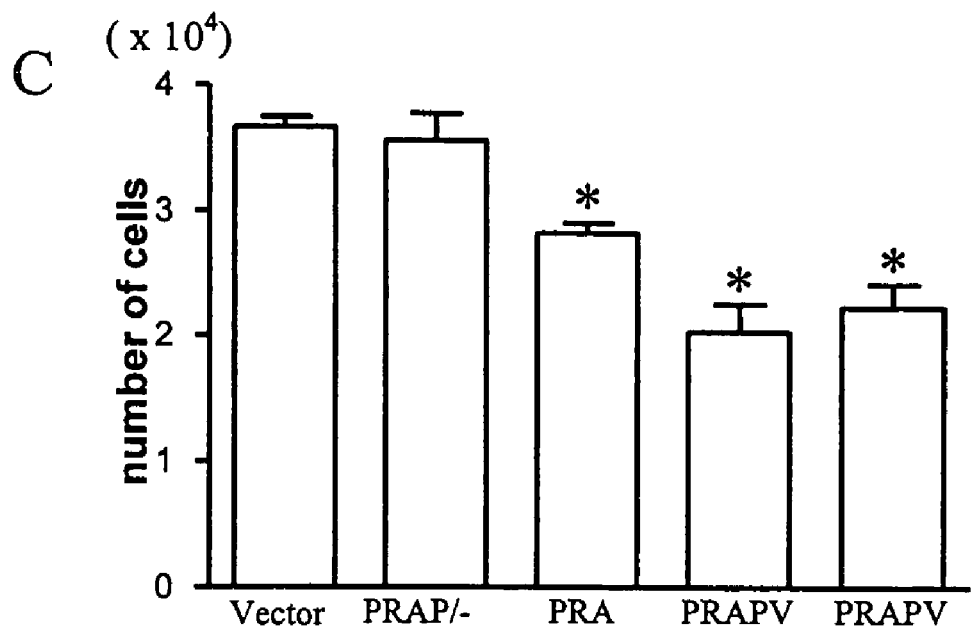
FIG. 9: Overexpression of PRAP and its expression in cell lines.
FIG. 9D shows Lanes 1-5 of Western blot showing the transfection of Vector, PRAP/-SP, PRAP, PRAPV1 and PRAPV2 in HeLa cells. GAPDH was used as an internal control.
Figure 9D:
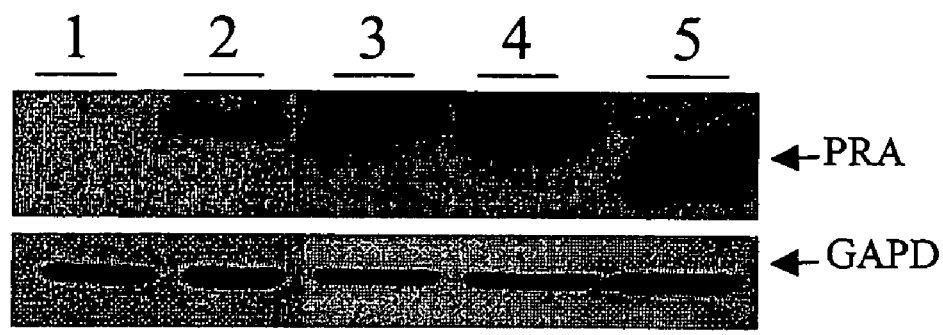

The overexpression of PRAP in HeLa cells significantly decreased cell numbers 48 and 72 h after transfection (FIG. 9A). The number of cells was reduced by 55% at 72 h compared to vector-transfected controls. Interestingly, transfection of truncated PRAP without signal peptide (PRAP/-SP) did not result in a reduction in cell numbers after 72 h. We also determined the effect of overexpressing PRAP and PRAP variants on cell numbers in both HeLa and HepG2 after 72 h (FIGS. 9B and C, respectively). Overexpression of PRAP and PRAP variants resulted in significant reductions in cell numbers of between 51-67% and 23-40% in HeLa and HepG2 cells, respectively, compared to vector-transfected controls. There was no significant difference between PRAP and the variants in cell numbers. The difference in response between HeLa and HepG2 likely represents the difference in transfection efficiencies. The overexpression of PRAP and PRAP variants in HeLa cells was confirmed by Western blot analysis (FIG. 9D).

Figure 10:
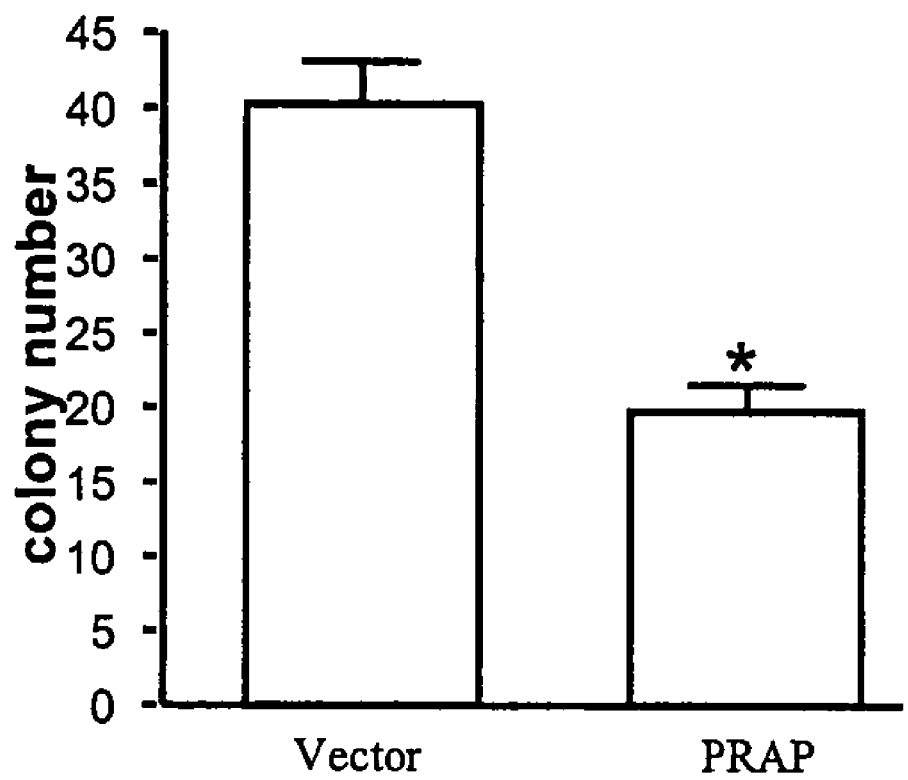
FIG. 10: Overexpression of PRAP on colony formation, Summary of colony formation assay in HeLa cells transfected with Vector or PRAP. Results shown are means of four separate wells. *, $P<0.01$ relative to vector controls using unpaired t test.

The effect of PRAP on the establishment and growth of colonies in HeLa cells was studied over a period of 3 weeks of selection in 1200 μg/ml of G418. The number of visible colonies on the plate was counted and the results of four separate transfections are summarized in FIG. 10. Transfection of PRAP resulted in a significant 50% reduction in the number of colonies. We also noted a reduction in the size of the PRAP-transfected colonies compared to controls.

Figure 11A:
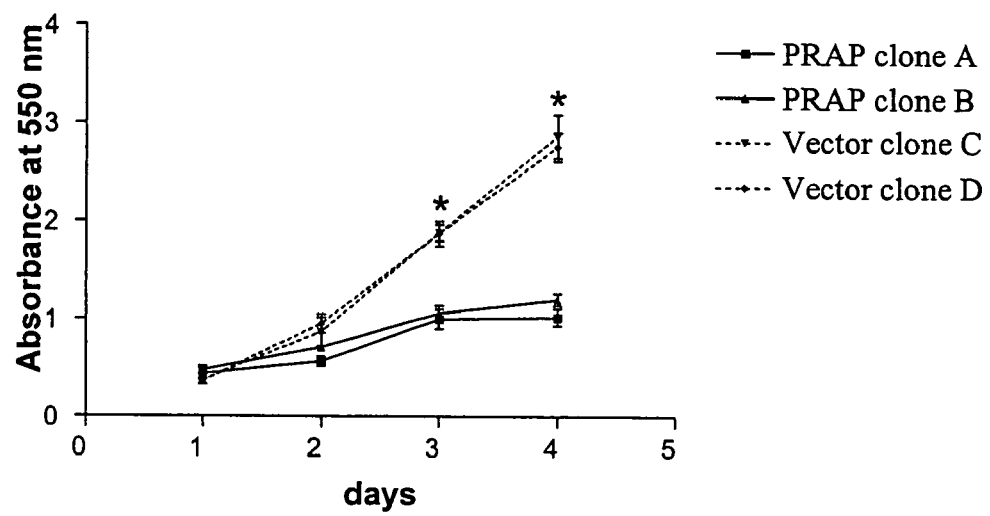
FIG. 11A shows a proliferation of PRAP stable clones as measured by MTT calorimetric assay.
Figure 11B:
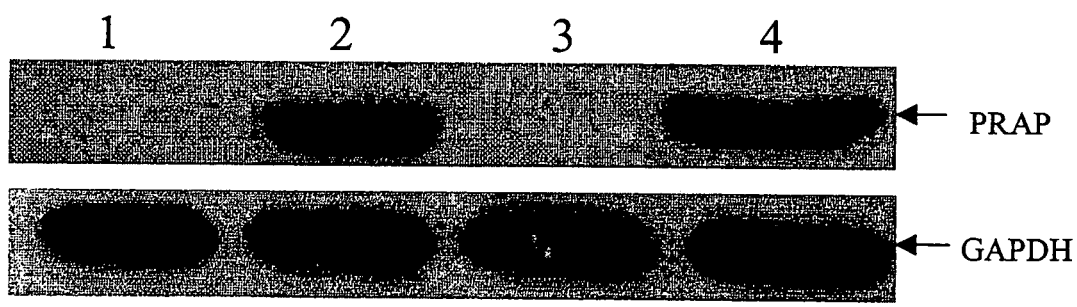
FIG. 11B is a representative Western blot showing expression of stable clones. Lanes 1 and 3, vector controls; Lanes 2 and 4, clones stably overexpressing PRAP. The bottom panel of FIG. 11B shows GAPDH control.

In a separate experiment, HT29 cells transfected with pcDNA 3.1/PRAP or pcDNA 3.1 vector were subjected to a similar selection. We selected 22 clones after 3 weeks and expanded them. Two clones were successfully expanded and retained overexpression of PRAP (FIG. 11B). We monitored the growth rate of these two clones in parallel with two stably transfected vector controls. Both the PRAP stably transfected clones showed a significantly lower rate of cell growth (p<0.01; FIG. 11A).

McrBC Digestion and PCR 250 ng of genomic DNA was digested using McrBC enzyme (New England Biolabs) at 37° C. for 2 hours. This enzyme cleaves a region on the DNA flanked by methylated cytosine 5' of Guanosine. Following digestion, control and enzyme-treated DNA was amplified using primers targeting the CG-rich regions.

Figure 13:
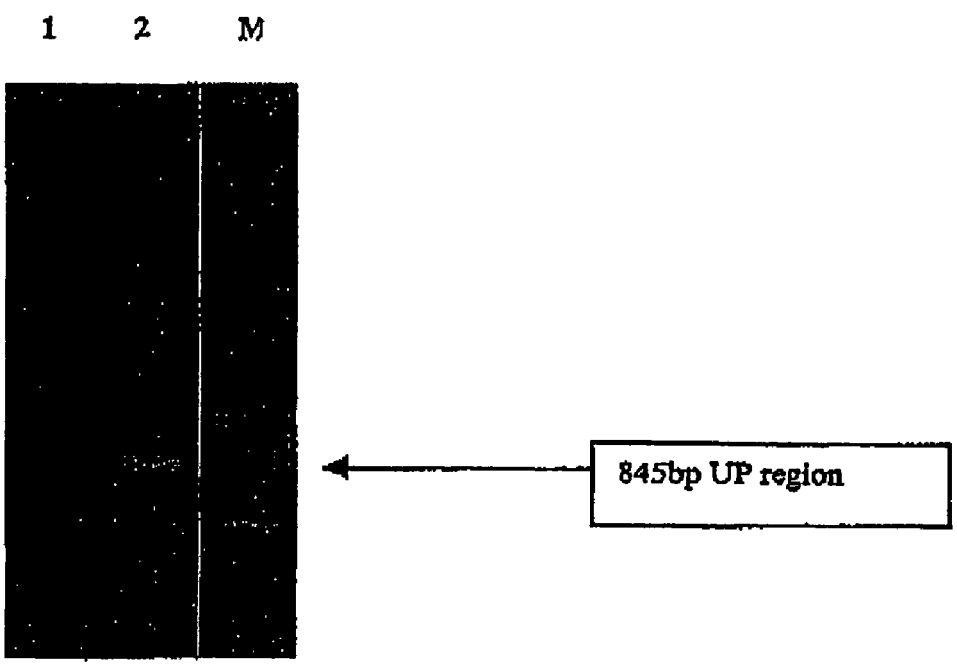
FIG. 13: Lane 1 is DNA digested with McrBC. Lane 2 is control DNA without McrBC treatment. Lane M is the marker.
Figure 14:
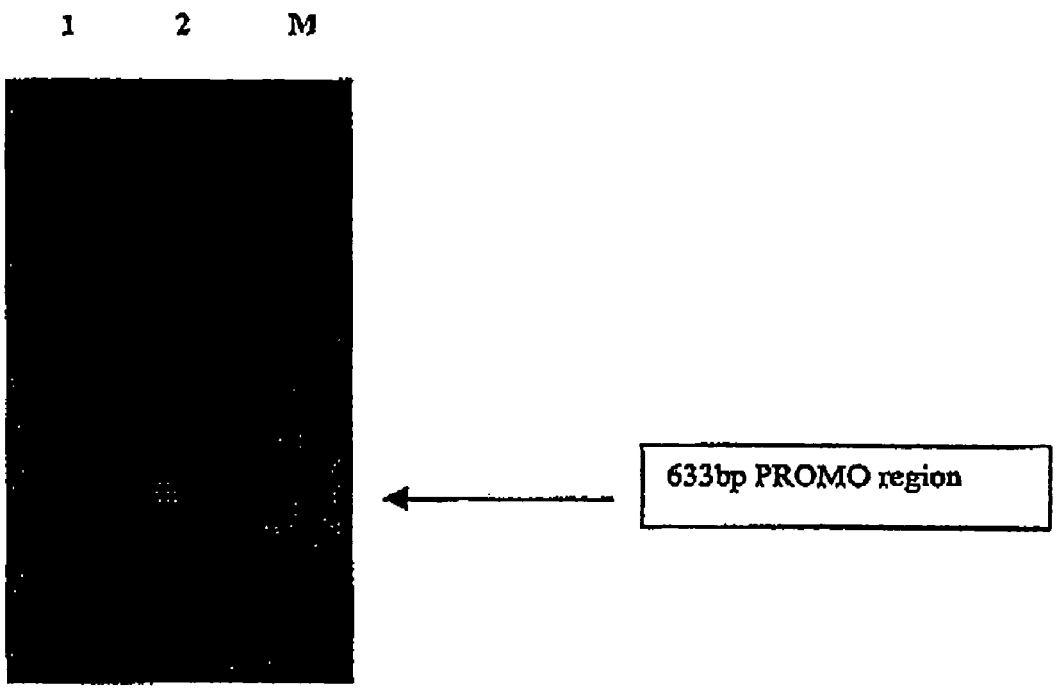
FIG. 14: Lane 1 shows the DNA digested with McrBC. Lane 2 shows the control DNA without McrBC treatment. And Lane M is the lane with the marker.

As shown in both FIGS. 13 and 14, both the UP and PROMO regions of the PRAP promoter contain methylated CG which resisted digestion with McrBC enzyme, hence allowing the amplification of a fragment of the DNA of expected size.

HpaII Digestion and PCR 250 ng of genomic DNA was digested with HpaII (New England Biolabs) at 37° C. overnight. This enzyme cleaves at the $2^{nd}$ cytosine of CCGG provided that the cytosine is unmethylated. Following digestion, control and enzyme-treated DNA was amplified using primers targeting the CG-rich regions.

Figure 15:
FIG. 15: Lanes 1 and 2 show DNA digested with Hpall while Lane 3 shows the control DNA without Hpall treatment.

As shown in FIG. 15, HpaII did not cut the DNA, suggesting that the cytosine was methylated.

Comment

As shown by the experimental results, upregulation of PRAP in vivo and in vitro translates to arrest of proliferation. This demonstrates that the promotion of PRAP expression in the cells leads to reduced proliferation in diseased state. At the same time, down-regulation of PRAP provides a means for stimulating proliferation. This is diametrically opposite to the finding and disclosure of U.S. Pat. No. 5,856,139 and US 2002/0115153.

REFERENCES

Augeron, C. and Laboisse, C. L. Emergence of permanently differentiated cell clones in a human colonic cancer cell line in culture after treatment with sodium butyrate. Cancer Res, 44: 3961-3969, 1984

Brownell, J. E. and Allis, C. D. Special HATs for special occasions: linking histone acetylation to chromatin assembly and gene activation. Curr Opin Genet Dev, 6: 176-184, 1996

Cameron, E. E., Bachman, K. E., Myohanen, S., Herman, J. G., and Baylin, S. B. Synergy of demethylation and histone deacetylase inhibition in the re-expression of genes silenced in cancer. Nat Genet, 21: 103-107, 1999

Chen, Z. J. and Pikaard, C. S. Epigenetic silencing of RNA polymerase I transcription: a role for DNA methylation and histone modification in nucleolar dominance. Genes Dev, 11: 2124-2136, 1997

Cress, W. D. and Seto, E. Histone deacetylases, transcriptional control, and cancer. J Cell Physiol, 184:1-16, 2000

Gray, S. G. and Ekstrom, T. J. The human histone deacetylase family. Exp Cell Res, 262: 75-83, 2001

Grunstein, M. Histone acetylation in chromatin structure and transcription. Nature, 389: 349-352, 1997

Hark, A. T., Schoenherr, C. J., Katz, D. J., Ingram, R. S., Levorse, J. M., and Tilghman, S. M. CTCF mediates methylation-sensitive enhancer-blocking activity at the H19/Igf2 locus. Nature, 405: 486-489, 2000

Heerdt, B. G., Houston, M. A., and Augenlicht, L. H. Short-chain fatty acid-initiated cell cycle arrest and apoptosis of colonic epithelial cells is linked to mitochondrial function. Cell Growth Differ, 8: 523-532, 1997

Hodin, R. A., Meng, S., Archer, S., and Tang, R. Cellular growth state differentially regulates enterocyte gene expression in butyrate-treated HT-29 cells. Cell Growth Differ, 7:647-653, 1996

Jenuwein, T. Re-SET-ting heterochromatin by histone methyltransferases. Trends Cell Biol, 11:266-273, 2001

Johnstone, R. W. Histone-deacetylase inhibitors: novel drugs for the treatment of cancer. Nat Rev Drug Discov, 1: 287-299, 2002

Jones, P. L., Veenstra, G. J., Wade, P. A., Vermaak, D., Kass, S. U., Landsberger, N., Strouboulis, J., and Wolffe, A. P. Methylated DNA and MeCP2 recruit histone deacetylase to repress transcription. Nat Genet, 19: 187-191, 1998

Kasik, J. and Rice, E. A novel complementary deoxyribonucleic acid is abundantly and specifically expressed in the uterus during pregnancy. Am J Obstet Gynecol, 176: 452-456, 1997

Kosugi, H., Towatari, M., Hatano, S., Kitamura, K., Kiyoi, H., Kinoshita, T., Tanimoto, M., Murate, T., Kawashima, K., Saito, H., and Naoe, T. Histone deacetylase inhibitors are the potent inducer/enhancer of differentiation in acute myeloid leukemia: a new approach to anti-leukemia therapy. Leukemia, 13: 1316-1324, 1999

Kramer, O. H., Gottlicher, M., and Heinzel, T. Histone deacetylase as a therapeutic target. Trends Endocrinol Metab, 12: 294-300, 2001

MacDonald, R. J., Swift, G. H., Przybyla, A. E., and Chirgwin, J. M. Isolation of RNA using guanidinium salts. Methods Enzymol, 152: 219-227, 1987

Marks, P. A., Richon, V. M., and Rifkind, R. A. Histone deacetylase inhibitors: inducers of differentiation or apoptosis of transformed cells. J Natl Cancer Inst, 92: 1210-1216, 2000

Marks, P., Rifkind, R. A., Richon, V. M., Breslow, R., Miller, T., and Kelly, W. K. Histone deacetylases and cancer: causes and therapies. Nat Rev Cancer, 1: 194-202, 2001

McBain, J. A., Eastman, A., Nobel, C. S., and Mueller, G. C. Apoptotic death in adenocarcinoma cell lines induced by butyrate and other histone deacetylase inhibitors. Biochem Pharmacol, 53:1357-1368, 1997

Nan, X., Ng, H. H., Johnson, C. A., Laherty, C. D., Turner, B. M., Eisenman, R. N., and Bird, A. Transcriptional repression by the methyl-CpG-binding protein MeCP2 involves a histone deacetylase complex. Nature, 393: 386-389, 1998

Nielsen, H., Engelbrecht, J., Brunak, S., and von Heijne, G. Identification of prokaryotic and eukaryotic signal peptides and prediction of their cleavage sites. Protein Eng, 10: 1-6, 1997

Plass, C., Shibata, H., Kalcheva, I., Mullins, L., Kotelevtseva, N., Mullins, J., Kato, R., Sasaki, H., Hirotsune, S., Okazaki, Y., Held, W. A., Hayashizaki, Y., and Chapman, V. M. Identification of Grf1 on mouse chromosome 9 as an imprinted gene by RLGS-M. Nat Genet, 14: 106-109, 1996

Robertson, K. D., Ait-Si-Ali, S., Yokochi, T., Wade, P. A., Jones, P. L., and Wolffe, A. P. DNMT1 forms a complex with Rb, E2F1 and HDAC1 and represses transcription from E2F-responsive promoters. Nat Genet, 25: 338-342, 2000

Santini, V., Kantarjian, H. M., and Issa, J. P. Changes in DNA methylation in neoplasia: pathophysiology and therapeutic implications. Ann Intern Med, 134: 573-586, 2001

Selker, E. U. Trichostatin A causes selective loss of DNA methylation in *Neurospora*. Proc Natl Acad Sci USA, 95: 9430-9435, 1998

Suzuki, H., Gabrielson, E., Chen, W., Anbazhagan, R., van Engeland, M., Weijenberg, M. P., Herman, J. G., and Baylin, S. B. A genomic screen for genes upregulated by demethylation and histone deacetylase inhibition in human colorectal cancer. Nat Genet, 31: 141-149, 2002

Tamaru, H. and Selker, E. U. A histone H3 methyltransferase controls DNA methylation in *Neurospora crassa*. Nature, 414: 277-283, 2001

Wang, Y., Cheong, D., Chan, S., and Hooi, S. C. Heparin/heparan sulfate interacting protein gene expression is up-regulated in human colorectal carcinoma and correlated with differentiation status and metastasis. Cancer Res, 59: 2989-2994, 1999

Wolffe, A. P. and Pruss, D. Targeting chromatin disruption: Transcription regulators that acetylate histones. Cell, 84: 817-819, 1996

Yamashita, K., Upadhyay, S., Osada, M., Hoque, M. O., Xiao, Y., Mori, M., Sato, F., Meltzer, S. J., and Sidransky, D. Pharmacologic unmasking of epigenetically silenced tumor suppressor genes in esophageal squamous cell carcinoma. Cancer Cell, 2: 485-495, 2002

Yoshida, M., Kijima, M., Akita, M., and Beppu, T. Potent and specific inhibition of mammalian histone deacetylase both in vivo and in vitro by trichostatin A. J Biol Chem, 265:17174-17179, 1990

Zhang, J., Rajkumar, N., and Hooi, S. C. Characterization and expression of the mouse pregnant specific uterus protein gene and its rat homologue in the intestine and uterus. Biochim Biophys Acta, 1492: 526-530, 2000

The invention claimed is:

1. A composition comprising an isolated polypeptide selected from the group consisting of:
   (a) polypeptides comprising sequence SEQ ID NO:4.

2. The composition of claim 1, further comprising a pharmaceutically acceptable substance selected from the group consisting of excipients, diluents, carriers and combinations thereof.

3. An isolated polypeptide selected from the group consisting of:
   polypeptides comprising the sequence SEQ ID NO:4.

* * * * *

SEQUENCE LISTING

```
<160> NUMBER OF SEQ ID NOS: 4

<210> SEQ ID NO 1
<211> LENGTH: 650
<212> TYPE: DNA
<213> ORGANISM: cDNA of PRAP
<220> FEATURE:
<221> NAME/KEY: CDS
<222> LOCATION: (74)..(529)

<400> SEQUENCE: 1
ggccgggtgc cagatactgg gatcagccac tgcagctccc tgagcactct ctacagagac    60
```

```
gcggacccca gac atg agg agg ctc ctc ctg gtc acc agc ctg gtg gtt      109
            Met Arg Arg Leu Leu Leu Val Thr Ser Leu Val Val
            1               5                   10 gtg ctg ctg tgg gag gca ggt gca gtc cca gca ccc aag gtc cct atc     157
Val Leu Leu Trp Glu Ala Gly Ala Val Pro Ala Pro Lys Val Pro Ile
        15                  20                  25 aag atg caa gtc aaa cac tgg ccc tca gag cag gac cca gag aag gcc     205
Lys Met Gln Val Lys His Trp Pro Ser Glu Gln Asp Pro Glu Lys Ala
    30                  35                  40 tgg ggc gcc cgt gtg gtg gag cct ccg gag aag gac gac cag ctg gtg     253
Trp Gly Ala Arg Val Val Glu Pro Pro Glu Lys Asp Asp Gln Leu Val
45                  50                  55                  60 gtg ctg ttc cct gtc cag aag ccg aaa ctc ttg acc acc gag gag aag     301
Val Leu Phe Pro Val Gln Lys Pro Lys Leu Leu Thr Thr Glu Glu Lys
                65                  70                  75 cca cga ggt cag ggc agg ggc ccc atc ctt cca ggc acc aag gcc tgg     349
Pro Arg Gly Gln Gly Arg Gly Pro Ile Leu Pro Gly Thr Lys Ala Trp
            80                  85                  90 atg gag acc gag gac acc ctg ggc cgt gtc ctg agc ccc gag ccc gac     397
Met Glu Thr Glu Asp Thr Leu Gly Arg Val Leu Ser Pro Glu Pro Asp
        95                  100                 105 cat gac agc ctg tac cac cct ccg cct gag gag gac cag ggc gag gag     445
His Asp Ser Leu Tyr His Pro Pro Pro Glu Glu Asp Gln Gly Glu Glu
    110                 115                 120 agg ccc cgg ttg tgg gtg atg cca aat cac cag gtg ctc ctg gga ccg     493
Arg Pro Arg Leu Trp Val Met Pro Asn His Gln Val Leu Leu Gly Pro
125                 130                 135                 140 gag gaa gac caa gac cac atc tac cac ccc cag tag ggctccaggg          539
Glu Glu Asp Gln Asp His Ile Tyr His Pro Gln
                145                 150 gccatcactg cccccgttct gttccaaagc ccaagctgtt gggactggga cccttcctac   599
cctgccccag ctagacaaat aaaccccaca ggccaaaaaa aaaaaaaaaa a            650

<210> SEQ ID NO 2
<211> LENGTH: 151
<212> TYPE: PRT
<213> ORGANISM: cDNA of PRAP

<400> SEQUENCE: 2

Met Arg Arg Leu Leu Leu Val Thr Ser Leu Val Val Leu Leu Trp
1               5                   10                  15

Glu Ala Gly Ala Val Pro Ala Pro Lys Val Pro Ile Lys Met Gln Val
            20                  25                  30

Lys His Trp Pro Ser Glu Gln Asp Pro Glu Lys Ala Trp Gly Ala Arg
        35                  40                  45

Val Val Glu Pro Pro Glu Lys Asp Asp Gln Leu Val Val Leu Phe Pro
    50                  55                  60

Val Gln Lys Pro Lys Leu Leu Thr Thr Glu Glu Lys Pro Arg Gly Gln
65                  70                  75                  80

Gly Arg Gly Pro Ile Leu Pro Gly Thr Lys Ala Trp Met Glu Thr Glu
                85                  90                  95

Asp Thr Leu Gly Arg Val Leu Ser Pro Glu Pro Asp His Asp Ser Leu
            100                 105                 110

Tyr His Pro Pro Pro Glu Glu Asp Gln Gly Glu Glu Arg Pro Arg Leu
        115                 120                 125

Trp Val Met Pro Asn His Gln Val Leu Leu Gly Pro Glu Glu Asp Gln
    130                 135                 140
```

```
Asp His Ile Tyr His Pro Gln
145                 150

<210> SEQ ID NO 3
<211> LENGTH: 152
<212> TYPE: PRT
<213> ORGANISM: Isoform of PRAP (V1)

<400> SEQUENCE: 3

Met Arg Arg Leu Leu Leu Val Thr Ser Leu Val Val Leu Leu Trp
1               5                   10                  15

Glu Ala Gly Ala Val Pro Ala Pro Lys Val Pro Ile Lys Met Gln Val
            20                  25                  30

Lys His Trp Pro Ser Glu Gln Asp Pro Glu Asn Arg Ala Trp Gly Ala
            35                  40                  45

Arg Val Val Glu Pro Pro Glu Lys Asp Asp Gln Leu Val Val Leu Phe
    50                  55                  60

Pro Val Gln Lys Pro Lys Leu Leu Thr Thr Glu Lys Pro Arg Gly
65                  70                  75                  80

Gln Gly Arg Gly Pro Ile Leu Pro Gly Thr Lys Ala Trp Met Glu Thr
                85                  90                  95

Glu Asp Thr Leu Gly His Val Leu Ser Pro Glu Pro Asp His Asp Ser
                100                 105                 110

Leu Tyr His Pro Pro Glu Glu Asp Gln Gly Glu Glu Arg Pro Arg
    115                 120                 125

Leu Trp Val Met Pro Asn His Gln Val Leu Leu Gly Pro Glu Glu Asp
    130                 135                 140

Gln Asp His Ile Tyr His Pro Gln
145                 150

<210> SEQ ID NO 4
<211> LENGTH: 142
<212> TYPE: PRT
<213> ORGANISM: Isoform of PRAP (V2)

<400> SEQUENCE: 4

Met Arg Arg Leu Leu Leu Val Thr Ser Leu Val Val Leu Leu Trp
1               5                   10                  15

Glu Ala Gly Ala Val Pro Ala Pro Lys Val Pro Ile Lys Met Gln Val
            20                  25                  30

Lys His Trp Pro Ser Glu Gln Asp Pro Glu Lys Ala Trp Gly Ala Arg
            35                  40                  45

Val Val Glu Pro Pro Glu Lys Asp Asp Gln Leu Val Val Leu Phe Pro
    50                  55                  60

Val Gln Lys Pro Lys Leu Leu Thr Thr Glu Lys Pro Arg Gly Thr
65                  70                  75                  80

Lys Ala Trp Met Glu Thr Glu Asp Thr Leu Gly His Val Leu Ser Pro
                85                  90                  95

Glu Pro Asp His Asp Ser Leu Tyr His Pro Pro Glu Glu Asp Gln
                100                 105                 110

Gly Glu Glu Arg Pro Arg Leu Trp Val Met Pro Asn His Gln Val Leu
            115                 120                 125

Leu Gly Pro Glu Glu Asp Gln Asp His Ile Tyr His Pro Gln
    130                 135                 140
```